(12) United States Patent
von Borstel et al.

(10) Patent No.: US 6,306,834 B1
(45) Date of Patent: Oct. 23, 2001

(54) ACYL DEOXYRIBONUCLEOSIDE DERIVATIVES AND USES THEREOF

(75) Inventors: Reid Warren von Borstel; Michael Kevin Bamat, both of Darnestown, MD (US)

(73) Assignee: Pro-Neuron, Inc.

( * ) Notice: Subject to any disclaimer, the term of this patent is extended or adjusted under 35 U.S.C. 154(b) by 0 days.

(21) Appl. No.: 08/479,516

(22) Filed: Jun. 7, 1995

Related U.S. Application Data

(62) Division of application No. 08/309,572, filed on Sep. 21, 1994, now Pat. No. 6,020,322, which is a continuation of application No. 08/149,469, filed on Nov. 9, 1993, now abandoned, which is a division of application No. 07/487,984, filed on Feb. 5, 1990, now abandoned, which is a continuation-in-part of application No. 07/115,923, filed on Oct. 28, 1987, now abandoned.

(51) Int. Cl.[7] .............................. A61K 31/70; C07H 19/00
(52) U.S. Cl. ................................. 514/45; 514/46; 514/49; 514/50; 536/27.1
(58) Field of Search ................................ 514/45, 46, 49, 514/50; 536/27.1

(56) References Cited

U.S. PATENT DOCUMENTS

| | | | |
|---|---|---|---|
| 3,585,188 | 6/1971 | Marumoto et al. | 536/28.53 |
| 3,894,000 | 7/1975 | Wechter et al. | 536/28.5 |
| 3,975,367 | 8/1976 | Gish et al. | 530/322 |
| 3,991,045 | 11/1976 | Ishida et al. | 536/28.51 |
| 4,048,432 | 9/1977 | Baker | 536/27.3 |
| 4,208,406 | 6/1980 | Lapinet et al. | 514/47 |
| 4,560,678 | 12/1985 | Ranson | 514/47 |
| 4,657,896 | 4/1987 | Yano et al. | 514/44 |
| 4,675,189 | 6/1987 | Kent et al. | 424/490 |
| 4,757,139 | 7/1988 | Kawaguchi et al. | 536/28.53 |
| 4,758,553 | 7/1988 | Ogoshi | 514/47 |
| 4,868,162 | 9/1989 | Kawaguchi | 514/50 |

FOREIGN PATENT DOCUMENTS

| | | |
|---|---|---|
| 1941942 | 3/1971 | (DE) . |
| 2147094 | 4/1973 | (DE) . |
| 3319282 | 11/1983 | (DE) . |
| 0056265 | 7/1982 | (EP) . |
| 0222192 | 5/1987 | (EP) . |
| 2096712 | 2/1972 | (FR) . |
| 2556727 | 6/1985 | (FR) . |
| 2023085 | 2/1977 | (JP) . |
| 0123917 | 9/1981 | (JP) . |
| 57-091995 | 6/1982 | (JP) . |
| 6049315 | 3/1983 | (JP) . |
| 58-167589 | 10/1983 | (JP) . |
| 8167598 | 10/1983 | (JP) . |
| 0028929 | 2/1985 | (JP) . |
| 60-064907 | 4/1985 | (JP) . |
| 60-174797 | 9/1985 | (JP) . |

OTHER PUBLICATIONS

Derwent Abstract No. 91–212578 of Japanese Publication JO 3135918 (Ajinomoto) (1991).
Chemical Abstracts, vol. 74, No. 112368K, Rajabalee, Angew. Chem. Int. Ed. Engl. 10(1):75 (1971).
Rosowsky et al, "Cancer Treatment Reports" 65:93–99 (Jan./Feb. 1981).
Kanazir et al, *Bull. Inst. Nuc. Sci. "Boris, Kidrich"* 9:145–153 (1959).
Beltz, et al, *Bioch. Biophys. Acta* 297:258–267 (1973).
Hunting, D.J., et al, *Carcinogenesis* 6:1525–1528 (1985).
Golba, et al, *Int. J. Rad. Biol.* 13:261–268 (1967).
Goh et al., *Proc. Soc. Exp. Biol. Med.* 145:938–943 (1974).
Horikawa, et al, *Exp. Cell Res.* 34:198–200 (1964).
Pantic, et al, *Nature* 193:993–994 (1962).
Paoletti, et al, *Rev. Fracais, Etudes Clin. et Bio.* 9:950–955 (1964).
Petrovic, et al, *Int. J. Radiat. Biol.* 18:243–258 (1970).
Petrovic, et al, *Studia Biophysica* 43:13–18 (1974).
Petrovic, et al, *Int. J. Radiat. Res.* 11:609–611 (1967).
Savkovic et al, *Nature* 203:1297–1298 (1964).
Savkovic et al, *Nature* 211:1179–1180 (1966).
Savkovic et al, *Int. J. Rad. Biol.* 9:361–368 (1965).
Smets, et al, *Int. J. Rad. Biol.* 13:269–273 (1967).
Soska et al, *Folia Biologica* 5:190–198 (1959).
Sugahara et al, Brookhaven Symposia in Biology, 284–302 (1967).
Wagner, *Int. J. Rad. Biol.*, 12:101–112 (1967).
Wilczok et al, *Int. J. rad. Biol.*, 9:201–211 (1965).
Goyanes–Villaescusa et al, *Lancet* 2:575–576 (1973).
Dumont, *Ann. Surg.* 150:799–807 (1959).
Nicolau et al, *Der Hautarzt*, 17:512–515 (1966).
Marshak et al, *Proc. Soc. Exp. Biol. Med.* 58:62–63 (1945).
Newman et al, *Am. J. Physiol.* 164:251–253 (1951).
Casida et al, *Biochemical Pharmacology* 15:627–644 (1966).
Hackh's Chemical Dictionary 3rd ed. Julius Grant, ed. pp. 44, 45, 332, 333.
Ensminger et al, *Biochemical Pharmacology*, 28: 1541–1545 (1979) thymidine 5"0–pivaloate.

(List continued on next page.)

*Primary Examiner*—Gary Geist
*Assistant Examiner*—Howard V. Owens, Jr.
(74) *Attorney, Agent, or Firm*—Nixon & Vanderhye

(57) ABSTRACT

The invention relates to compositions comprising acyl derivatives of 2'-deoxyribonucleosides. The invention also relates to methods of treating or preventing radiation, mutagen and sunlight-induced biological damage, and methods for improving wound healing and tissue repair, comprising administering the compositions of the present invention to an animal.

25 Claims, 4 Drawing Sheets

OTHER PUBLICATIONS

Ensminger et al, the Chemical Abstracts, 92: 87921x (1980).

Narang et al, the Chemical Abstracts, 83:147700a (1975).

Adamiak et al, the Chemical Abstracts, 106: 156803g (1987).

Pfleiderer, the Chemical Abstracts, 107: 218016j (1987).

Nair et al, the Chemical Abstracts, 101: 192382z (1984).

Ishido et al, the Chemical Abstracts, 92: 59149h (1980).

Fridovich, *Annu. Rev. Biochem.,* 44:147–159 (1975).

Biochemistry, vol. 13, No. 3, Jan. 29, 1974, pp. 553–559; M.J. Robins et al: "3"–0–aminoacyl–2"–deoxyadenosines and 2"–0–aminoacyl–3"–deoxyadenosines related to charged transfer ribonucleic acid termini.

Biochemistry, vol. 14, No. 14, Jul. 15, 1974, pp. 3144–3151; S.P. Dutta et al: Synthesis and properties of the naturally occurring N–[(9–beta–D–ribofuranosylpurin–6–yl)–N–methylcarbamoyl]–L–threonine (mt6A) and other related synthetic analogs.

Biochemistry, vol. 20, No. 1, Jan. 6, 1981, pp. 8–15, American Chemical Society; A. Bhuta et al: "Stereochemical control of ribosomal peptidyltransferase reaction. Role of amino acid side–chain orientation of acceptor substrate".

Biochemistry, vol. 20, No. 12, Jun. 9, 1981, pp. 3480–3485, American Chemical Society; K. Quiggle et al: "Donor Site of Ribosomal Peptidyltransferase: Investigation of Substrate specificity using 2"(3")–0–(N–acylaminoacyl)dinucleoside phosphates as models of the 3"terminus of N–acylaminoacyl transfer ribonucleic acid".

Journal of American Chemical Society, vol. 104, No. 2, 1982, pp. 544–547, American Chemical Society; G. Buchi et al: "Photochemical epoxidation of aflatoxin B1 and sterigmatocystin: Synthesis of Guanine–Containing adducts".

Pure and Applied Chemistry, vol. 52, No. 12, 1980, pp. 2705–2715, IUPAC GB; T. Matsuura et al: "Organic Chemical Approach to Photo–Cross–Links of Nucleic Acids to Proteins".

Journal of Carbohydrate Nucleosides. Nucleotides, vol. 4, No. 6, 1977, pp. 387–408, Marcel Dekker, Inc.; E.K. Ryu et al; "Aminoacyl Derivatives of Nucleosides, Nucleotides, and Polynucleotides. XXVII. General Synthesis of 2"(3")–O–Aminoacyl Dinucleoside Phosphates Derived from the AA–tRNA terminus".

Morrison and Boyd, Fourth Edition, "Organic Chemistry", Allyn and Bacon, Inc., Boston, 1983.

Leukemia, 2(10) 109–110 (1988).

Blood, 74(6) 1923–1928 (1989).

Cancer Treatment Reports, 69(7–8), 851–857 (1985).

ACYL DEOXYRIBONUCLEOSIDE DERIVATIVES AND USES THEREOF

This is a Divisional of application Ser. No. 08/309,572, filed Sep. 21, 1994 now U.S. Pat. No. 6,020,322, which is a Continuation of Ser. No. 08/149,469, filed Nov. 9, 1993 now abandoned, which is a Divisional of Ser. No. 07/487,984, filed Feb. 5, 1990, abandoned, which is a CIP of Ser. No. 07/115,923, filed Oct. 28, 1987 now abandoned.

FIELD OF THE INVENTION

This invention relates generally to acyl derivatives of deoxyribonucleosides and to the use of those derivatives to deliver exogenous deoxyribonucleosides to animal tissue. More specifically, this invention relates to the acyl derivatives of 2'-deoxyadenosine, 2'-deoxyguanosine, 2'-deoxycytidine and 2'-deoxythymidine and the use of those novel derivatives to deliver the deoxyribonucleosides to animal tissue and thereby to support cellular metabolic functions. Even more specifically, this invention relates to the use of the novel acyl derivatives to treat or prevent a variety of physiological and pathological conditions in cell tissue, including damage by radiation, sunlight, mutagens, wounds, and other conditions.

BACKGROUND OF THE INVENTION

There are fundamentally two possible chemical or biochemical approaches to attenuating the deleterious effects of ionizing radiation on organisms:

(1) attenuation of initial damage to biological structures, and (2) improvement or acceleration of recovery.

A number of compounds are known that provide some protection from ionizing radiation when they are present in the body during irradiation. Such compounds are typically antioxidants or free-radical scavengers that inactivate reactive chemical species formed during irradiation before they can damage important biological structures. Prominent examples of radioprotective compounds include cysteamine, 2-beta-amino-ethyl-isothiouronium-Br-HBr (AET), and S-2-(3-aminopropylamino) ethyl phosphorothioic acid (WR-2721). Since these compounds must be introduced into the organism before or during irradiation, they are obviously not useful in situations of unexpected or accidental exposure. Moreover, these compounds are toxic in humans.

The main possibilities for effective chemical therapy in organisms in which irradiation has already occurred are:

(1) to promote repair and recovery of individual cells within the organism, or (2) to accelerate or enhance proliferation and/or differentiation of surviving stem cells.

Bone marrow and intestinal epithelium are among the tissues most sensitive to radiation damage; attempts to promote recovery from irradiation need to focus on the stem cells in these tissues.

There exist several agents which can improve the survival of irradiated mammals when administered after irradiation. These include the yeast-derived polysaccharide Glucan, and polypeptide cytokines such as Interleukin-1, Granulocyte-Colony Stimulating Factor, and Granulocyte/Macrophage-Colony Stimulating Factor; all of these agents improve bone-marrow stem cell proliferation or differentiation. However, their efficacy is modest, producing Dose Reduction Factors less than 1.1 when administered after irradiation has already occurred, and their use is complicated by side effects. Moreover, they are all macromolecules which can only be administered parenterally.

There exists a need for compounds which effectively promote recovery when administered after exposure to ionizing radiation and which have important pharmaceutical qualities such as nontoxicity and activity after oral administration. Such agents would be useful in the cases of accidental exposure to ionizing radiation, and also in conjunction with radiation therapy for cancer, in order to promote recovery of normal tissue from irradiation. Such agents may also improve recovery from certain forms of chemical damage, e.g., bone-marrow suppression following either accidental or therapeutic exposure to compounds like cyclophosphamide or busulfan, which are both used in cancer chemotherapy.

It has been demonstrated that administration of exogenous deoxyribonucleic acid (DNA) to experimental animals after exposure to ionizing radiation can result in improved survival and functional recovery. Kanazir et al., Bull. Inst. Nuc. Sci. "Boris Kidrich" 9:145–153 (1959); Wilczok, T., et al., Int. J. Rad. Biol. 9:201–211 (1965); Golba, S., et al., Int. J. Rad. Biol. 13:261–268 (1967); U.S. Pat. No. 3,803,116.

Studies in cell cultures in vitro suggest that the actual restorative agents are deoxyribonucleosides, the enzymatic degradation products of DNA. Petrovic, D., et al., Int. J. Rad. Biol. 18:243–258 (1970). However, depolymerized DNA or deoxyribonucleosides administered to animals were ineffective in promoting survival or recovery after irradiation. Kanazir et al., Bull. Inst. Nuc. Sci. "Boris Kidrich" 9:145–153 (1959). There is reason to believe that this apparent contradiction is due to the rapid catabolism of deoxyribonucleosides in vivo by the enzymes in plasma and various organs. Thus, after administration of deoxyribonucleosides to rodents, tissues are exposed to effective concentrations for less than five minutes. Beltz et al., Bioch. Biophys., Acta. 297:258–267 (1973). In cell cultures, optimum survival after irradiation was found when deoxyribonucleosides were present in the culture medium for at least three hours. When DNA is administered parenterally, it is probably gradually depolymerized to give a sustained release of free deoxyribonucleosides into the circulation.

There may be other physiological or pathological conditions of mammalian tissue wherein the supply of exogenous deoxyribonucleosides may have therapeutic applications. Newman et al., Am. J. Physiol. 164:251–253 (1951), disclose a study in rats subjected to partial hepatectomy. The course of liver regeneration was followed for eleven days. The livers of rats treated with DNA regenerated significantly faster than did livers of untreated animals. It is likely that deoxyribonucleosides were the actual active agents in this study, since DNA is a large molecule that is not taken up efficiently by mammalian cells. Similarly, DNA applied to dermal wounds has been found to accelerate some aspects of the healing process, e.g., formation of granulation tissue. Dumont, Ann. Surg. 150:799–807 (1959); Marshak et al., Proc. Soc. Exp. Biol. Med. 58:62–63 (1945); Nicolau et al., Der Hautartzt 17:512–515 (1966). Yane and Kitano, U.S. Pat. No. 4,656,896, disclose evidence of beneficial effects of parenterally administered DNA in the treatment of gastric ulcers in rats.

In these examples, it is likely that the effect of DNA was related to its gradual degradation, resulting in the release of deoxyribonucleosides over a prolonged period. DNA is not, however, a suitable pharmaceutical agent to administer to humans, either orally or parenterally. In the case of oral administration, nucleosides released from DNA would mainly be degraded by enzymes in the intestinal lumen, in the intestinal walls, in plasma, and in the liver, rather than being available to tissues. Problems with parenterally administered DNA include possible antigenicity (exacerbated by adhering proteins which are difficult to remove during extraction), nonuniformity between batches, and possible undesirable effects not related to nucleoside release, e.g., enhancement of interferon release from lymphocytes, which is a known effect of double-stranded nucleic acid.

The administration of deoxyribonucleosides has heretofore been contemplated for the reversal of obvious deficiencies of deoxyribonucleotides (e.g., thymidine administration to reverse toxicity caused by methotrexate, an antineoplastic agent which inhibits thymidine nucleotide biosynthesis; administration of deoxycytidine to reverse arabinosyl cytosine toxicity, or in people with deficiencies of particular enzymes (e.g., purine nucleoside phosphorylase) that ultimately result in impaired deoxyribonucleotide synthesis). Thymidine administration has also been considered as an antineoplastic treatment, since, in high concentrations, thymidine has cytostatic or cytotoxic properties.

However, the invention disclosed herein pertains to the recognition that unexpected beneficial effects may be obtained after administration of supraphysiological quantities of mixtures of deoxyribonucleosides in such a manner that they are available to tissues for a sustained period; this goal may be best accomplished through the use of the deoxyribonucleoside derivatives of the invention.

OBJECTS OF THE INVENTION

While the strategy of delivering DNA and/or deoxyribonucleosides to physiologically or pathologically damaged tissue has been recognized, the art has heretofore failed to provide satisfactory methods for introducing deoxyribonucleosides in sufficiently high and reliable amounts in vivo to successfully treat the pathological and physiological conditions and to promote cellular repair and survival of the animal. Moreover, although a variety of compounds have been developed which protect animals against some effects of ionizing radiation or chemical mutagens, deoxyribonucleosides provided to tissues for a sufficient time have the greatest clinical potential for post-exposure treatment of such damage. Clinical implementation of this strategy, however, awaits development of satisfactory and convenient methods for delivering adequate quantities of deoxyribonucleosides to tissues in vivo. Similarly, full appreciation and clinical implementation of the capacity of deoxyribonucleosides to promote wound healing or tissue repair awaits development of satisfactory methods for their delivery to tissues in vivo.

It is thus a primary object of this invention to identify pharmaceutically acceptable compounds which can efficiently be used to deliver pharmacologically effective amounts of deoxyribonucleosides or their respective derivatives to animal tissue.

It is still a further object of this invention to provide a family of deoxyribonucleoside derivatives which can be effectively administered orally or parenterally, which have minimal toxicity, and which can be administered to animals and humans to effectively promote cellular repair in a number of physiological and pathological conditions and to promote survival of the animal when administered after exposure to radiation has occurred.

It is still a further and related object of this invention to provide certain derivatives of 2'-deoxyadenosine, 2'-deoxyguanosine, 2'-deoxycytidine, and 2'-deoxythymidine which, when administered to an animal, will deliver those deoxyribonucleosides to the animal tissue.

It is a related object of this invention to substantially improve the bioavailability of 2'-deoxyadenosine, 2'-deoxyguanosine, 2'-deoxycytidine, and 2'-deoxythymidine by enhancing the transport of these deoxyribonucleosides across the gastrointestinal tract and other biological membranes.

It is still a further and more specific object of this invention to provide a family of deoxyribonucleoside derivatives for the treatment of a variety of liver, bone, skin, hematological, and other pathological and physiological conditions.

It is still a further object of this invention to provide deoxyribonucleoside derivatives and methods for using those derivatives which are safe, inexpensive, and which accelerate the normal cellular processes of regeneration and healing.

SUMMARY OF THE INVENTION

These and other objects of the invention are achieved by the administration of certain acyl derivatives of 2'-deoxyadenosine, 2'-deoxyguanosine, 2'-deoxycytidine, and 2'-deoxythymidine. These acyl derivatives can be used to prevent or treat radiation, sunlight and mutagen-induced cellular damage, to improve the healing of wounds, or repair damaged tissues, and in the treatment of other physiological and pathological tissue conditions.

While the prior art discloses some acylated derivatives of deoxyribonucleosides, their substituents (e.g., pivaloate, isobutyrate, benzoate, or adamantoate) were selected for properties related to utility as protecting groups in chemical synthesis (e.g., of oligonucleotides), and are not generally acceptable for administration to animals. The novel compounds disclosed herein are preferred because of their nontoxic substituents. These present minimal hazard to the organism to which they are administered and can be selected to yield desirable pharmaceutical and pharmacological properties without undue experimentation.

Acylated derivatives of some antineoplastic and antiviral nucleoside analogs have been utilized as prodrugs of these cytotoxic agents. However, very different biochemical and physiological issues are involved in improving the therapeutic index of toxic nucleoside analogs versus the delivery of the nontoxic deoxyribonucleosides in appropriate quantities and combinations for improving tissue repair or regeneration, as in the present invention.

A major aspect of the invention is the recognition that acyl derivatives of deoxyribonucleosides, particularly when derivatives of two or more deoxyribonucleosides are combined, have unexpected therapeutic properties. This is evidenced in the data concerning survival of irradiated mice. The invention also includes novel classes of derivatives that are particularly desirable in terms of both efficacy and safety.

Broadly, the acyl derivatives of 2'-deoxyadenosine are those having the formula (I)

(I)

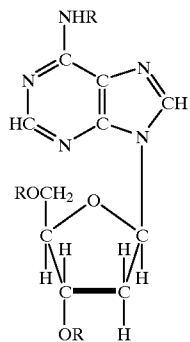

wherein R is hydrogen or an acyl radical of a metabolite other than acetyl, with the proviso that at least one R is not hydrogen, or a pharmaceutically acceptable salt thereof.

The preferred acyl derivatives of 2'-deoxyadenosine are those having the formula (I)

(I)

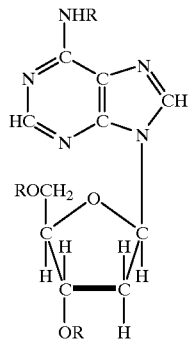

wherein R is H or an acyl group derived from a carboxylic acid selected from one or more of the group consisting of pyruvic acid, lactic acid, enolpyruvic acid, an amino acid, a fatty acid other than acetic acid, lipoic acid, nicotinic acid, pantothenic acid, succinic acid, fumaric acid, p-aminobenzoic acid, betahydroxybutyric acid, orotic acid, and carnitine, with the proviso that at least one R is not hydrogen, or a pharmaceutically acceptable salt thereof.

Broadly, the acyl derivatives of 2'-deoxyguanosine are those having the formula (II)

(II)

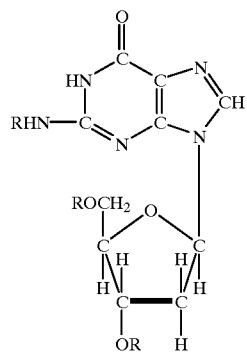

wherein R is hydrogen or an acyl radical of a metabolite other than acetyl, with the proviso that at least one R is not hydrogen, or a pharmaceutically acceptable salt thereof.

The preferred acyl derivatives of 2'-deoxyguanosine are those having the formula (II)

(II)

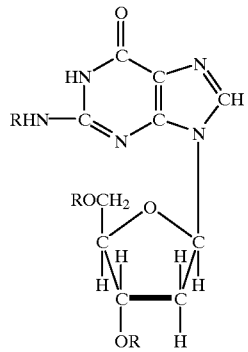

wherein R is H or an acyl group derived from a carboxylic acid selected from one or more of the group consisting of pyruvic acid, lactic acid, enolpyruvic acid, an amino acid, a fatty acid other than acetic acid, lipoic acid, nicotinic acid, pathothenic acid, succinic acid, fumaric acid, p-aminobenzoic acid, betahydroxybutyric acid, orotic acid, and carnitine, with the proviso that at least one R is not hydrogen, or a pharmaceutically acceptable salt thereof.

Broadly, the acyl derivatives of 2'-deoxycytidine are those having the formula (III)

(III)

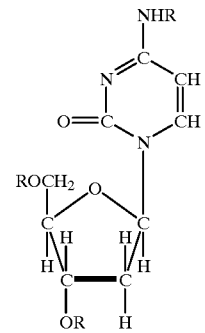

wherein R is hydrogen or an acyl radical of a metabolite other than acetyl, with the proviso that at least one R is not hydrogen, or a pharmaceutically acceptable salt thereof.

The preferred acyl derivatives of 2'-deoxycytidine are those having the formula (III)

(III)

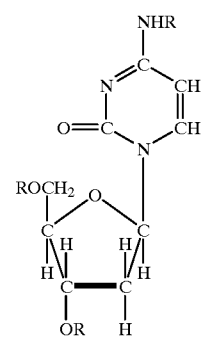

wherein R is H or an acyl group derived from a carboxylic acid selected from one or more of the group consisting of pyruvic acid, lactic acid, enolpyruvic acid, an amino acid, a fatty acid other than acetic acid, lipoic acid, nicotinic acid, pantothenic acid, succinic acid, fumaric acid, p-aminobenzoic acid, betahydroxybutyric acid, orotic acid, and carnitine, with the proviso that at least one R is not hydrogen, or a pharmaceutically acceptable salt thereof.

Broadly, the acyl derivatives of 2'-deoxythymidine are those having the formula (IV)

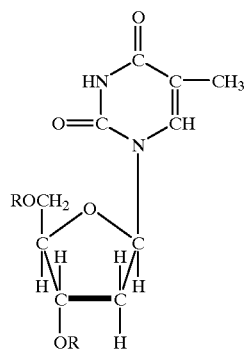

(IV)

wherein R is hydrogen or an acyl radical of a metabolite other than a fatty acid having less than five carbon atoms, with the proviso that at least one R is not hydrogen, or a pharmaceutically acceptable salt thereof.

The preferred acyl derivatives of 2'-deoxythymidine are those having the formula (IV)

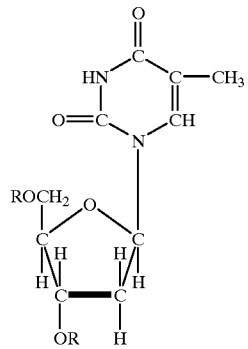

(IV)

wherein R is H or an acyl group derived from a carboxylic acid selected from one or more of the group consisting of pyruvic acid, lactic acid, enolpyruvic acid, an amino acid, a fatty acid containing 5 or more carbon atoms, lipoic acid, nicotinic acid, pantothenic acid, succinic acid, fumaric acid, p-aminobenzoic acid, betahydroxybutyric acid, orotic acid and carnitine, with the proviso that at least one R substituent is not hydrogen, or a pharmaceutically acceptable salt thereof.

The acyl derivatives of 2'-deoxythymidine may also be those having the formula (V)

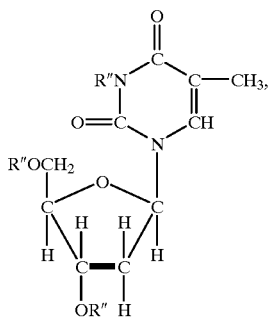

(V)

wherein R" is hydrogen or an acyl radical of a metabolite, with the proviso that the R" on nitrogen is not hydrogen, or a pharmaceutically acceptable salt thereof.

Preferred acyl derivatives of 2'-deoxythymidine are those having the formula (V)

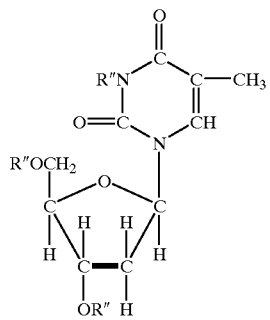

(V)

wherein R" is H or an acyl group derived from a carboxylic acid selected from one or more of the group consisting of pyruvic acid, lactic acid, enolpyruvic acid, an amino acid, a fatty acid, lipoic acid, nicotinic acid, pantothenic acid, succinic acid, fumaric acid, p-aminobenzoic acid, betahydroxybutyric acid, orotic acid, and carnitine, with the proviso that the R" on nitrogen is not hydrogen, or a pharmaceutically acceptable salt thereof.

The invention also includes compounds having formulae I–IV wherein the ribose moiety is monoacylated at the 3' or 5' position with the derivative of a fatty acid and includes 3',5'-diacylated derivatives of compounds I–IV wherein at least one such substituent is derived from a fatty acid having 5 or more carbon atoms.

The acyl derivatives of 2'-deoxyadenosine, 2'-deoxyguanosine, 2'-deoxycytidine, and 2'-deoxythymidine having formulae I, II, III, and V, desirably are substituted with an acyl derivative of a carboxylic acid having 3–22 carbon atoms.

Where acyl derivatives of any of the compounds of formulae I–V are substituted by an acyl group derived from an amino acid, the amino acid is desirably selected from the group consisting of glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, and hydroxylysine.

In a preferred embodiment of the invention, a mixture of at least two acyl derivatives of 2'-deoxyadenosine, 2'-deoxyguanosine, 2'-deoxycytidine, and 2'-deoxythymidine is used. Said compositions contain an effective amount of each of at least two compounds selected from at least two of the groups of compounds having the formulae

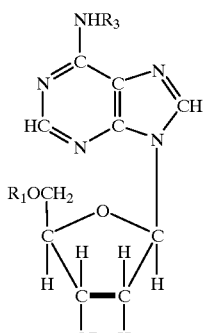

(I)

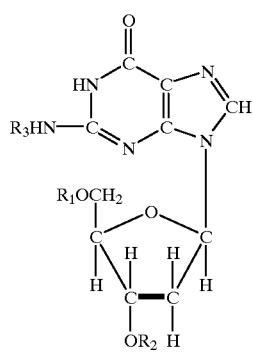

(II)

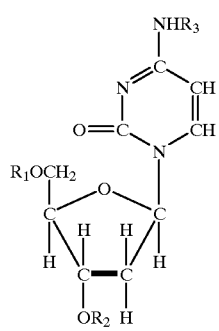

(III)

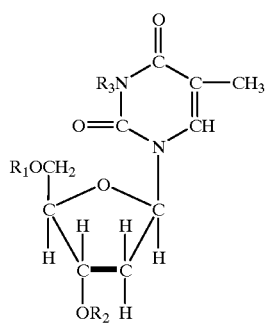

(IV)

wherein $R_1$, $R_2$, and $R_3$ are the same or different and each is H or an acyl group derived from a carboxylic acid, provided that at least one of said substituents $R_1$, $R_2$, and $R_3$ in each of said groups of compounds is not hydrogen, or pharmaceutically acceptable salts thereof. In a preferred embodiment, $R_1$, $R_2$, and $R_3$ are the same or different and each is H or an acyl group derived from a carboxylic acid selected from the group consisting of an amino acid, an unbranched fatty acid containing 2 to 22 carbon atoms, a dicarboxylic acid containing 3 to 22 carbon atoms, and an optionally substituted benzoyl or heterocyclic aromatic carboxylic acid that is substantially nontoxic. Preferred optionally substituted benzoyl or heterocyclic carboxylic acids include nicotinic acid, and p-aminobenzoic acid.

In another preferred embodiment of the invention, a composition comprising a mixture of an effective amount of at least three compounds selected from at least three of the groups of compounds having the formulae I–IV, shown above, is used. In still another preferred embodiment, a composition comprising a mixture of an effective amount of at least four compounds selected from at least four of the groups of compounds having the formulae I–IV, shown above, is used.

Further substantial benefits may be obtained, particularly where the compositions of the invention are used to ameliorate the effects of radiation, if a radioprotective compound is included together with one or more of the acyl deoxyribonucleosides. The radioprotective compounds may be those selected from the group consisting of WR-2721, NAC, DDC, cysteamine, 2-mercaptoethanol, mercaptoethylamine dithiothreitol, glutathione, 2-mercaptoethanesulfonic acid, WR-1065, nicotinamide, 5-hydroxytryptamine, 2-beta-aminoethyl-isothiouronium-Br-Hbr, glucans, GLP/B04, GLP/B05, OK-432, Biostim, PSK, Lentinan, Schizophyllan, Rhodexman, Levan, Mannozym, MVE-2, MNR, MMZ, IL-1, TNF, thymic factor TF-5, glutathione peroxidase, superoxide dismutase, catalase, glutathione reductase, glutathione transferase, selenium, $CdCl_2$, $MnCl_2$, Zn acetate, Vitamin A, beta carotene, prostaglandins, tocopherol, methylene blue and PABA.

The invention is also embodied in pharmaceutical compositions which comprise one or more of the novel deoxyribonucleosides together with a pharmaceutically acceptable carrier. In addition, known acetyl derivatives of the 2'-deoxyadenosine, 2'-deoxyguanosine, 2'-deoxycytidine and 2'-deoxythymidine as well as the fatty acid derivatives of thymidine wherein the acyl group contains 3 or 4 carbon atoms may be used alone, in combination with one another or in combination with one or more novel compounds, in pharmaceutical compositions of the invention. The composition may further include a radioprotective compound as described. The compositions may be in the form of a liquid, a suspension, a tablet, a dragee, an injectable solution, a topical solution, or a suppository.

A skin lotion may be advantageously prepared by combining an effective amount of one or more of the acyl deoxyribonucleosides of the invention together with a suitable carrier. Such a skin lotion advantageously contains from 0.1 to 5 percent by weight of the deoxyribonucleosides and, if desirable, the radioprotective compound.

The pharmaceutical compositions of the invention can also be embodied in bioerodible microcapsules, the microcapsules desirably being selected from the group consisting of polylactate or lactate-glycolate copolymers.

It is believed that the delivery of exogenous deoxyribonucleosides to the tissue of an animal can be effectively achieved by administering to that animal an effective amount of an acyl derivative of a deoxyribonucleoside of formulae I–V. By enhancing the delivery of exogenous deoxyribonucleosides, and thereby increasing their bioavailability, it may be possible to treat physiological or pathological conditions of the tissues of an animal by essentially supporting some metabolic functions thereof. Without being bound by theory, the invention may work, as well, by increasing the bioavailability of nucleoside anabolites, e.g., nucleotides or nucleotide-derived cofactors. Administration of the nucleosides per se increases their bioavailability but, due to rapid extracellular catabolism, this may not result in sustained elevation of cellular nucleotide levels. At lower nucleoside levels there is rapid uptake and utilization by the cells whereas at higher levels there is saturation and the excess is degraded. The invention is believed to work by delivering a sustained supply of nucleoside at lower levels.

The specific conditions where advantages may be achieved using the compounds, compositions, and methods of the invention include situations where improvement of DNA repair or improvement of stem cell differentiation and proliferation are useful. Such conditions particularly include: (1) treating or preventing damage due to ionizing or ultraviolet irradiation; (2) improving restoration of hematopoiesis in the case of diminished bone marrow function due to ionizing radiation, chemical damage (e.g., side effects of anticancer or antiviral treatments), or disease; and (3) accelerating regeneration and repair of various damaged tissues, e.g., in healing of wounds and burns, or in promoting regeneration of damaged liver tissue. In treating all of these conditions, a compound of the invention, with or without additional carriers, radioprotective compounds, and other adjuvants, is administered to an animal, in particular, a human.

Administration of the acylated derivatives offers certain advantages over the nonderivatized compounds. The acyl substituents can be selected to increase the lipophilicity of the nucleoside, thus improving its transport from the gastrointestinal tract into the bloodstream. The acylated derivatives are effective when administered orally and may be applied topically in some situations. The acylated derivatives are resistant to catabolism by nucleoside deaminases and nucleoside phosphorylases in the intestine, liver, other organs, and the bloodstream. Thus, administration of the acylated derivatives of the invention, either orally, parenterally, or topically, allows sustained delivery of desirable combinations and quantities of deoxyribonucleosides to the tissues of an animal, since the acyl substituents are gradually removed by enzymes (esterases and peptidases) in plasma and tissues, releasing free deoxyribonucleosides over time.

dT=2'-deoxythymidine
dC=2'-deoxycytidine
dG=2'-deoxyguanosine
dA=2'-deoxyadenosine.

Figure 2:
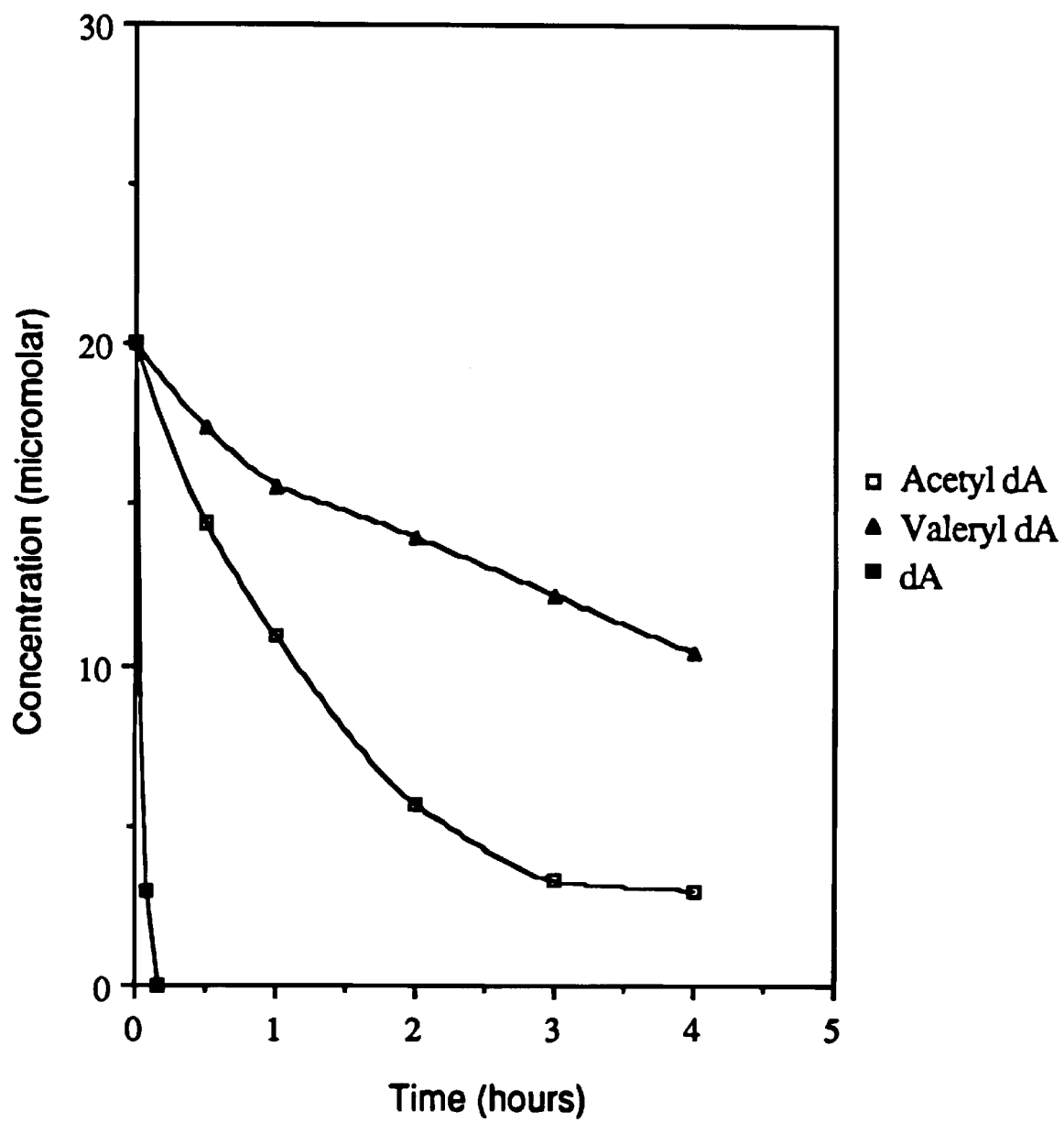

FIG. 2 is a graph illustrating the rapid cetabolism of deoxyadenosine, and the gradual deacylation of adenosine derivatives (to yield deoxyadenosine) in plasma.

Figure 3:
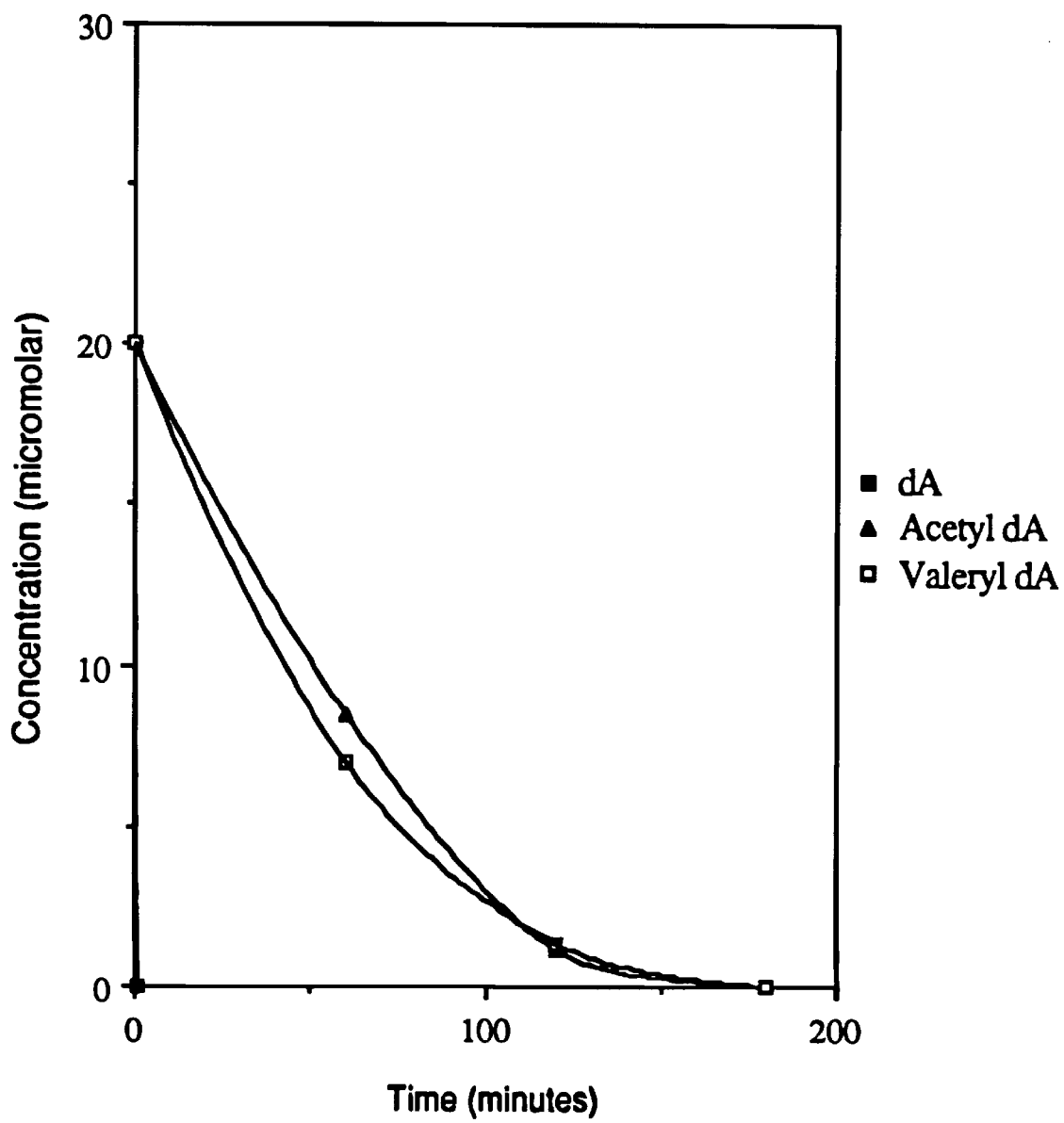

FIG. 3 is a graph illustrating the rapid catabolism of deoxyadenosine derivatives (to yield deoxyadenosine) in liver extract.

Figure 4:
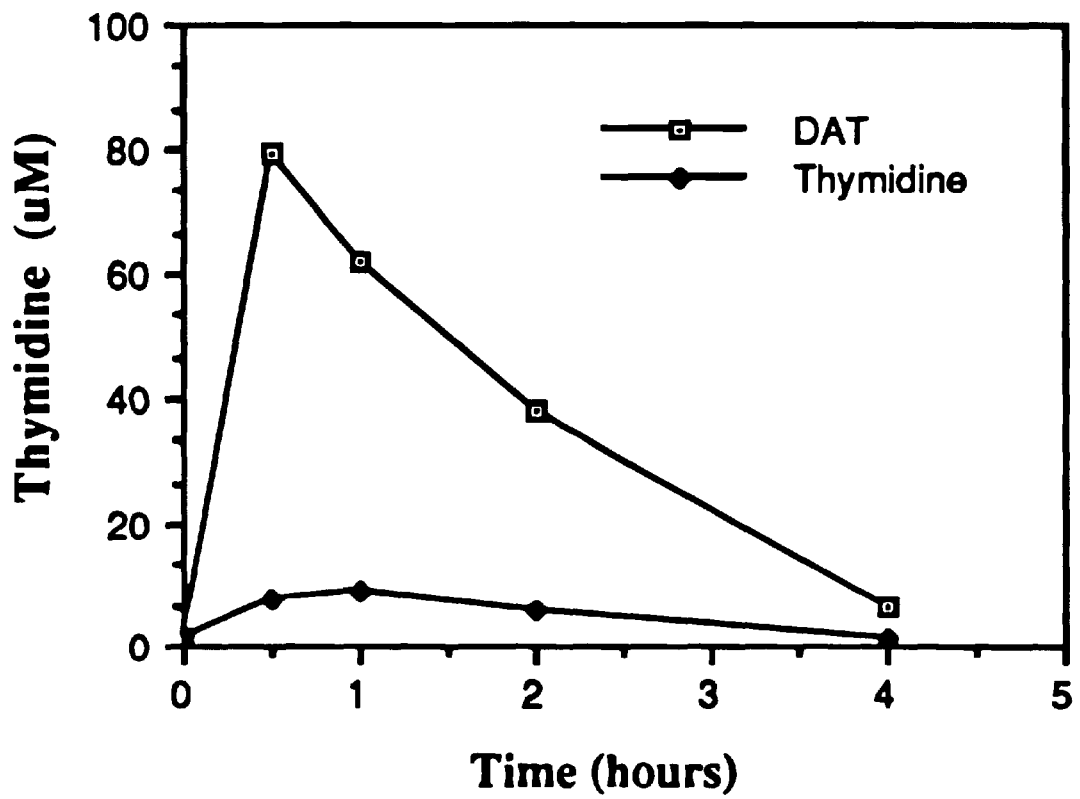

FIG. 4 is a graph illustrating plasma thymidine concentrations after oral administration of thymidine or di-O-acetylthymidine to rats.

DESCRIPTION OF THE PREFERRED EMBODIMENTS

A "metabolite" is a chemical compound that is formed by, or participates in, a metabolic reaction. In the context of this application, metabolites include not only carboxylic acids known to be synthesized within the human body, but also naturally occurring (but perhaps synthesized rather than extracted) carboxylic acids that might be derived from other animal or plant sources. The limiting criteria are that the compound should be substantially nontoxic and biocompatible, and should readily enter into metabolic pathways in vivo, so as to present essentially no toxicity during long-term consumption in the doses proposed. It is preferable that the compounds be metabolized rather than excreted intact (or conjugated through detoxification reactions), as concentration of carboxylic acids within the kidney may lead to undesirable excessive acidity. Therefore, carboxylic acids that normally or easily participate in intermediary, catabolic, or anabolic metabolism are preferred substituents.

The term "pharmaceutically acceptable salts" means salts with pharmaceutically acceptable acid addition salts of the deoxyribonucleoside derivatives, which include, but are not limited to, sulfuric, hydrochloric, or phosphoric acids.

The term "coadministered" means that at least two of the acylated derivatives of the invention are administered during a time frame wherein the respective periods of pharmacological activity overlap.

"Acyl derivatives" means derivatives of a 2'-deoxyribonucleoside in which a substantially nontoxic organic acyl substituent derived from a carboxylic acid is attached to one or more of the free hydroxyl groups of the ribose moiety of the deoxyribonucleoside with an ester linkage and/or where such a substituent is attached to a primary or secondary amine in the pyrimidine ring of deoxycytidine or deoxythymidine, or in the purine ring of deoxyadenosine or deoxyguanosine, with an amide linkage. Such acyl substituents are derived from carboxylic acids which include, but are not limited to, compounds from the group consisting of lactic acid, an amino acid, a fatty acid, nicotinic acid, dicarboxylic acids, p-aminobenzoic acid, and orotic acid. Preferred acyl substituents are compounds which are normally present in the body, either as dietary constituents or as intermediary metabolites, which are essentially nontoxic when cleaved from the deoxyribonucleoside in vivo.

"Amino acids" include, but are not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids.

"Fatty acids" are aliphatic carboxylic acids having 2–22 carbon atoms. Such fatty acids may be saturated, partially saturated or polyunsaturated.

"Dicarboxylic acids" are fatty acids with a second carboxylic acid substituent.

Preferred acyl derivatives of 2-deoxyribonucleosides for enhancing transport across biological membranes are those which are more lipophilic than are the parent nucleosides. In general, lipophilic acyl nucleoside derivatives have acyl substituents which are nonpolar (aside from the carboxylate group). Lipophilic acyl substituents include especially groups derived from fatty acids containing 2 to 22 carbon atoms. One of ordinary skill in the art can determine whether a particular acyl-substituted nucleoside derivative is more lipophilic than the underivatized nucleoside using standard techniques, i.e., comparison of the partition coefficients determined in water-octanol mixtures.

Following passage of the acylated nucleoside derivative from the gastrointestinal tract into the bloodstream, or across other biological membranes, the acyl substituents are cleaved by plasma and tissue esterases (or amidases) to give the free nucleosides. The preferred acyl groups of the invention are naturally occurring metabolites in the body, or are compounds which readily enter intermediary metabolic pathways. Thus they offer little toxicity when released in vivo by endogenous esterases or amidases.

It is also possible to prepare acyl nucleoside derivatives which contain both polar and nonpolar acyl substituents. The polar acyl group will retard passage of the nucleoside derivative from the gastrointestinal tract, allowing for a more sustained delivery of the compound into the bloodstream after a single dose. The polar group may be cleaved by esterases, amidases, or peptidases present in the intestinal tract to give a nucleoside with a nonpolar acyl substituent which may then efficiently enter the circulation. Polar acyl substituents may be chosen by one of ordinary skill in the art, without undue experimentation, which are cleaved at a faster rate than are nonpolar acyl substituents. Preferred such substituents are basic amino acids (lysine or arginine), acidic amino acids (glutamate or aspartate), or dicaboxylic acids.

For parenteral injection, acyl derivatives with polar substituents, which are therefore water soluble yet resistant to premature degradation or elimination, may also be used with advantage.

Preferred Compounds of the Invention

The preferred compounds of the invention are (1) acyl derivatives of 2'-deoxyadenosine, having the formula

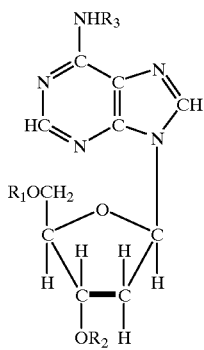

wherein $R_1$, $R_2$, and $R_3$ may be the same or different and each is hydrogen or an acyl group derived from (a) an unbranched fatty acid with 3 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid having 3 to 22 carbon atoms, provided that
  (i) not all of $R_1$, $R_2$, and $R_3$ are H, and
  (ii) where $R_3$ is not H, then $R_1$ and/or $R_2$ may also be acetyl, or a pharmaceutically acceptable salt thereof;

(2) acyl derivatives of 2'-deoxyguanosine having the formula

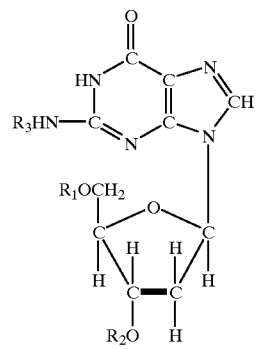

wherein $R_1$, $R_2$, and $R_3$ may be the same or different and each is hydrogen or an acyl group derived from (a) an unbranched fatty acid with 3 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid having 3 to 22 carbon atoms, provided that
  (i) not all of $R_1$, $R_2$, and $R_3$ are H, and
  (ii) where $R_3$ is not H, then $R_1$ and/or $R_2$ may also be acetyl, or a pharmaceutically acceptable salt thereof;

(3) acyl derivatives of 2'-deoxycytidine, having the formula

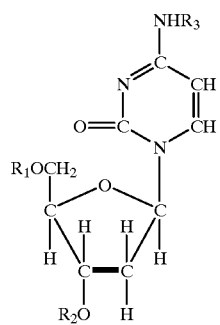

wherein $R_1$, $R_2$, and $R_3$ may be the same or different and each is hydrogen or an acyl group derived from (a) an unbranched fatty acid with 3 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid having 3 to 22 carbon atoms, provided that
  (i) not all of $R_1$, $R_2$, and $R_3$ are H, and
  (ii) where $R_3$ is not H, then $R_1$ and/or $R_2$ may also be acetyl, or a pharmaceutically acceptable salt thereof;

(4) acyl derivatives of 2'-deoxythymidine, having the formula

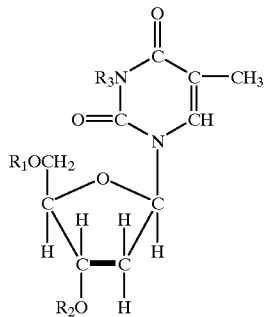

wherein $R_1$ is an acyl group derived from (a) an unbranched fatty acid with 3 to 15 or 17 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid having 3 to 22 carbon atoms, and $R_2$ and $R_3$ are H, or a pharmaceutically acceptable salt thereof;

(5) acyl derivatives of 2'-deoxythymidine, having the formula

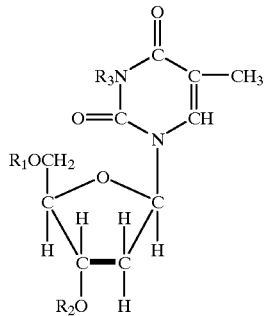

wherein $R_1$ is H, $R_2$ is an acyl group derived from (a) an unbranched fatty acid with 3 to 13 or 15 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, and ornithine,
(c) nicotinic acid, or
(d) a dicarboxylic acid with 3 to 22 carbon atoms, and $R_3$ is H or a pharmaceutically acceptable salt thereof;

(6) acyl derivatives of 2'-deoxythymidine, having the formula

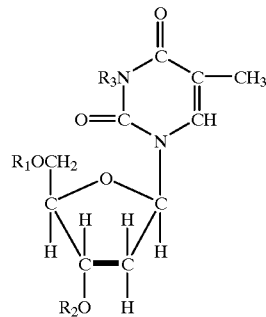

wherein $R_1$ and $R_2$ may be the same or different and each is an acyl group derived from (a) an unbranched fatty acid with 5 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid with 3 to 22 carbon atoms,
and $R_3$ is H, or a pharmaceutically acceptable salt thereof; and (7) acyl derivatives of 2'-deoxythymidine, having the formula

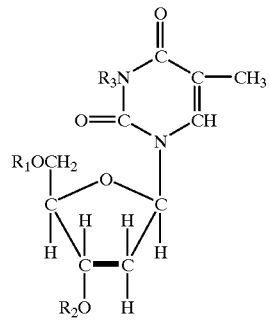

wherein $R_1$ and $R_2$ are the same or different and each is an acyl group derived from (a) an unbranched fatty acid with 2 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid with 3 to 22 carbon atoms, and $R_3$ is an acyl group derived from an optionally substituted benzoyl or heterocyclic carboxylic acid that is substantially nontoxic, or a pharmaceutically acceptable salt thereof.

The preferred acyl derivatives of 2'-deoxyadenosine are those wherein $R_1$ is an acyl group derived from an unbranched fatty acid with 6 to 16 carbon atoms, $R_2$ is H or an acyl group derived from an unbranched fatty acid with 6 to 16 carbon atoms, and $R_3$ is H or an acyl group derived from an amino acid with an acidic or basic side chain.

The preferred acyl derivatives of 2'-deoxyguanosine are those wherein $R_1$ is an acyl group derived from an unbranched fatty acid with 6 to 16 carbon atoms, $R_2$ is H or an acyl group derived from an unbranched fatty acid with 6 to 16 carbon atoms or an amino acid with an acidic or basic side chain, and $R_3$ is H or an acyl group derived from an amino acid with an acidic or basic side chain.

The preferred acyl derivatives of 2'-deoxycytidine are these wherein $R_1$ is an acyl group derived from an unbranched fatty acid with 6 to 16 carbon atoms, $R_2$ is H or an acyl group derived from an unbranched fatty acid with 6 to 16 carbon atoms, and $R_3$ is H or an acyl group derived from an amino acid with an acidic or basic side chain.

The preferred acyl derivatives of 2'-deoxythymidine (4) are those wherein $R_1$ is acyl group derived from an unbranched fatty acid with 6 to 15 carbon atoms.

The preferred acyl derivatives of 2'-deoxythymidine (5) are those wherein $R_2$ is an acyl group derived from an unbranched fatty acid with 16 carbon atoms.

The preferred acyl derivatives of 2'-deoxythymidine (6) are those wherein $R_1$ and $R_2$ are the same or different and each is an acyl group derived from an unbranched fatty acid with 6 to 16 carbon atoms.

The preferred acyl derivatives of 2'-deoxythymidine (7) are those wherein $R_1$ and $R_2$ are the same or different and each is an acyl group derived from an unbranched fatty acid with 6 to 16 carbon atoms and $R_3$ is an acyl group derived from nicotinic acid, benzoic acid, or para-aminobenzoic acid.

Therapeutic Uses

The lipophilic acyl deoxyribonucleoside derivatives of the invention are useful for enhancing the transport of the deoxyribonucleosides across biological membranes including the gastrointestinal tract in animals and thereby increase the bioavailablity of the deoxyribonucleosides. Foremost among such animals are humans; however, the invention is not intended to be so limited, it being within the contemplation of the invention to treat all animals which may experience a beneficial effect from the administration of the acyl deoxyribonucleosides of the invention.

The compositions of the present invention may be administered to an animal either before or after exposure to radiation, sunlight or mutagens. The acyl derivative form of the deoxyribonucleosides provides an orally effective means for delivery of deoxyribonucleosides to tissues. These derivatives may also be given parenterally or topically. Administration of the derivatives avoids the problem of rapid catabolism by gastrointestinal, liver and plasma enzymes.

Figure 1:
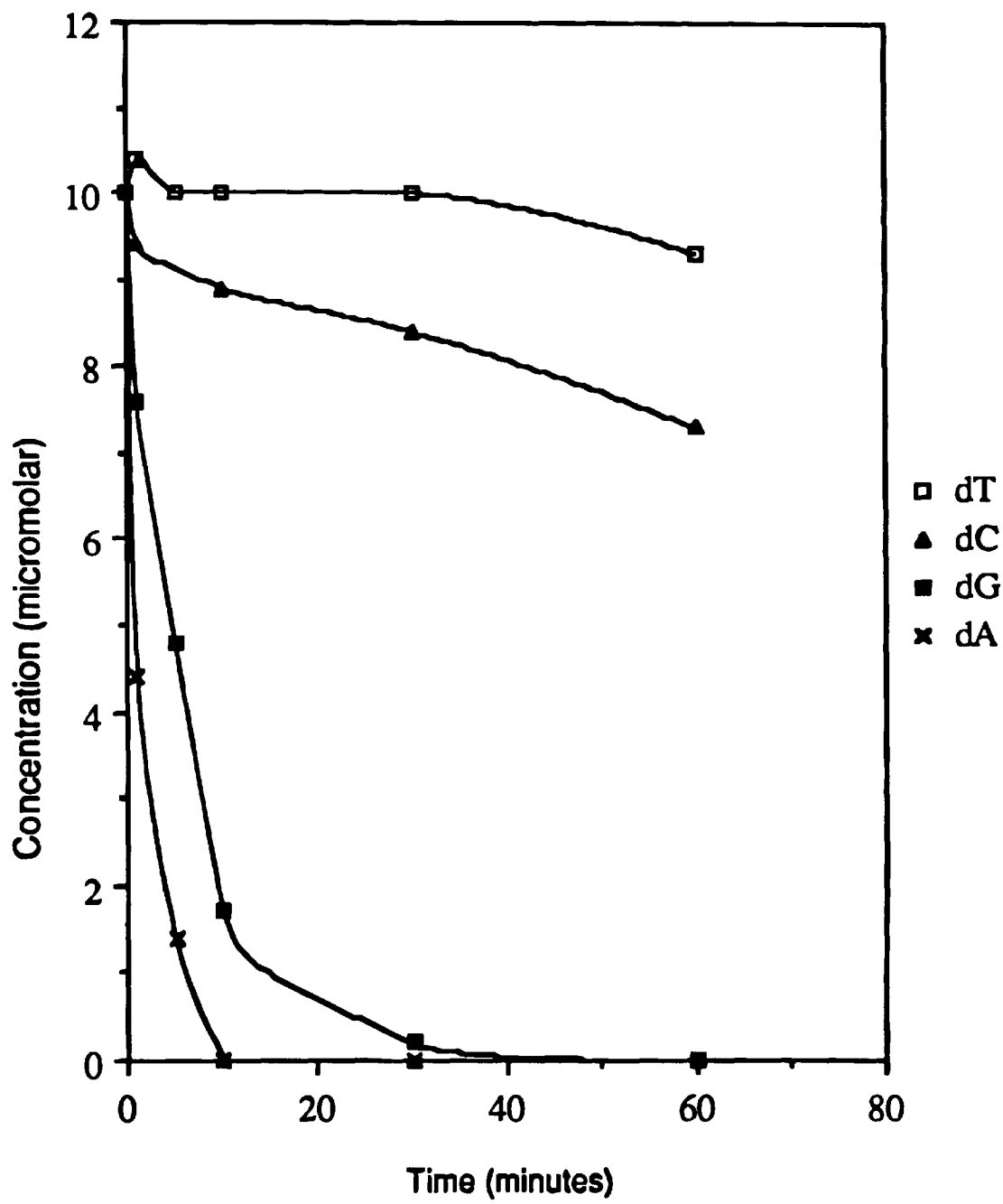
FIG. 1 is a graph illustrating the rates of degradation of deoxyribonucleosides in plasma. The following abbreviations are used.

As shown in FIG. 1, free deoxyguanosine (dG) and deoxyadenosine (dA) are degraded in plasma extremely rapidly.

The fates of deoxyadenosine, 5'-O-acetyldeoxyadenosine, and 5'-O-valeryldeoxyadenosine in plasma are shown in FIG. 2. Each of these compounds was added to separate aliquots of rat plasma, at initial concentrations of 20 micromolar. The plasma was sampled at various time points, and the desired compounds were assayed by liquid chromatography.

Deoxyadenosine (dA) is very rapidly degraded in plasma, disappearing within 10 minutes. Administration of this compound to an animal or human subject would make deoxyadenosine available to tissues for a very short period of time.

5'-O-acetyldeoxyadenosine and 5'-O-valeryldeoxyadenosine are, however, deacylated in plasma (to form deoxyadenosine) over a period of several hours. Therefore, administration of either of these compounds would result in prolonged availability of deoxyadenosine to tissues.

The fates of deoxyadenosine, 5'-O-acetyldeoxyadenosine, and 5'-O-valeryldeoxyadenosine in liver extract are shown in FIG. 3. Each of these compounds was added to separate aliquots of an aqueous extract of rat liver, at initial concentrations of 20 micromolar. The extract was sampled at various time points, and the desired compounds were assayed by liquid chromatography.

Deoxyadenosine (dA) is extremely rapidly degraded in plasma, disappearing within 1 minute. The initial degradation product is deoxyinosine, which is not directly reutilizable by tissues. Administration of deoxyadenosine per se to an animal or human subject would make deoxyadenosine available to tissues for only a very short period of time.

5'-O-acetyldeoxyadenosine and 5'-O-valeryldeoxyadenosine are, however, deacylated in liver extract (to form deoxyadenosine) over a period of more than 1 hour. Therefore, administration of either of these compounds would result in prolonged availability of deoxyadenosine to liver or other organs.

Thus a mixture of several different acyl derivatives of each deoxyribonucleoside in an administered dose may be selected to provide optimal bioavailability. A composition containing 3',5'-diacetyl-2'-deoxycytidine, and 5'-palmitoyl-2'-deoxycytidine (and corresponding derivatives of other deoxyribonucleosides) provides a more prolonged bioavailability of nucleosides after a single dose than does administration of a single acyl derivative of each nucleoside. Thus, after administration of the mixture described above, the acetylated compound is relatively rapidly deacetylated, yielding free deoxycytidine (or other desired deoxyribonucleosides) shortly after administration. The 5'-palmitoyl derivative is deacylated more slowly, providing additional free deoxycytidine after the deoxycytidine derived from 3',5'-diacetyl-2'-deoxycytidine has been metabolized by tissues.

The acyl deoxyribonucleoside composition may be formulated as part of a suntan lotion that may be applied before or after exposure to sunlight. The suntan lotion may also comprise one or more sun blockers such as PABA, esters of PABA, and other non-PABA chemical sunscreens. The acyl deoxynucleotides are absorbed by the skin and taken up by cells. The acyl deoxyribonucleosides are then cleaved by tissue esterases to give free deoxyribonucleosides in amounts effective for repair of sunlight-induced damage. The combination of the acyl deoxyribonucleoside compositions and a sun blocker such as PABA offers maximal protection of the skin from the sun.

The acyl deoxyribonucleoside compositions of the invention also find use in ameliorating some of the effects of aging by providing a high and sustained level of deoxyribonucleosides to enhance the natural DNA repair processes of cells, and thereby, treating the naturally occurring progressive accumulation of damage of DNA which occurs on aging. Compositions for treatment or amelioration of the effects of aging may be applied topically, in the form of a skin lotion, or may be administered orally or parenterally.

There are conditions other than radiation damage in which exogenous deoxyribonucleosides or derivatives thereof have useful therapeutic applications.

Deoxyribonucleic acid has been used to accelerate wound cicatrization or healing, and also to accelerate liver regeneration in experimental animals. It is likely that in these situations, as well as in the situations where DNA is used to promote survival after irradiation of animals, the DNA is serving as a storage depot for deoxyribonucleosides, which gradually releases the deoxyribonucleotides and deoxyribonucleosides during enzymatic degradation.

Administration of acylated deoxyribonucleosides, as described herein, as a method of delivering deoxyribonucleosides to tissues which is preferable to the administration of foreign DNA for the purpose of improving wound healing or tissue regeneration. Unlike DNA, acylated deoxyribonucleosides are effective after oral administration; they are also nonantigenic and are much easier to purify then DNA.

The composition of the present invention may also be administered to enhance the healing of damage tissue. Such damaged tissue includes skin wounds (e.g., punctures, lacerations, abrasions, etc.), burned tissue (skin, etc.), diseased or damaged liver (from surgery or other wounds of the liver, or from cirrhosis or diabetes, etc.), damaged heart muscle (e.g., improved scar formation after myocardial infarction), and damaged bone marrow (e.g., after radiation treatment or chemotherapeutic treatment).

For the purpose of treating skin wounds or burns, the compositions may be applied topically as part of a skin lotion or cream, or as part of a bioerodible polymer.

Preferred acyl substituent groups on the hydroxyl groups of the deoxyribose ring of 2'-deoxyadenosine, 2'-deoxycytidine, 2'-deoxyguanosine, and thymidine are fatty acids with 6 to 16 carbon atoms, or dicarboxylic acids with 4 to 6 carbon atoms, e.g., succinic, glutaric, or adipic acids. Preferred substituents on the exocyclic amine groups of deoxycytidine, deoxyadenosine, and deoxyguanosine are amino acids with basic side chains, e.g., lysine or arginine. Preferred substituents on the secondary amine in the tymine ring of thymidine are nicotinic acid or para-aminobenzoic acid.

Preferred deoxyadenosine derivatives comprise $N^6$-lysyl-5'-palmitoyl deoxyadenosine, 5'-palmitoyl adenosine, $N^6$-lysyl-5'-dodecanoyl deoxyadenosine, 5'-dodecanoyl adenosine, and $N^6$-lysyl-3',5'-diacetyl deoxyadenosine.

Preferred deoxyguanosine derivatives comprise $N^2$-lysyl-5'-palmitoyl deoxyguanosine, 5'-dodecanoyl deoxyguanosine, and $N^2$-lysyl-3',5'-diacetyl deoxyguanosine.

Preferred deoxycytindine derivatives comprise $N^4$-lysyl-5'-palmitoyl deoxycytidine, 5'-palmitoyl deoxycytidine, $N^4$-lysyl-5'-dodecanoyl deoxycytidine, 5'-dodecanoyl deoxycytidine, and $N^4$-lysyl-3',5'-acetyl deoxycytidine.

Preferred thymidine derivatives comprise $N^3$nicotinoyl-5'-palmitoyl thymidine, 5'-palmitoyl thymidine, $N^3$-nicotinoyl-5'-dodecanoyl thymidine, 5'-dodecanoyl thymidine, and $N^3$-nicotinoyl-3',5'-acetyl thymidine.

Compositions within the scope of the invention include those which contain mixtures of the acyl derivatives of the deoxyribonucleosides in amounts effective to achieve its intended purpose. Such compositions may contain 0 to 50 mole percent of the acyl derivative of deoxycytidine, 0 to 50 mole percent of the acyl derivative of deoxyguanosine, 0 to 50 mole percent of the acyl derivative of deoxythymidine and 0 to 50 mole percent of the acyl derivative of doexyadenosine, with the proviso that the total content of the acyl deoxyribonucleosides adds up to 100 mole percent.

A preferred composition contains 25 mole percent of the acyl derivative of deoxycytidine, 25 mole percent of the acyl derivative of deoxyguanosine, 25 mole percent of the acyl derivative of deoxythymidine, and 25 mole percent of the acyl derivative of deoxyadenosine.

For treatment of radiation-induced cellular damage or sunburn, or to enhance wound healing, preferred dosages include amounts of the acyl derivatives equivalent to 10 to 1000 mg of 2'-deoxyadenosine, 10 to 1000 mg of 2'-deoxyguanosine, 10 to 1000 mg of 2'-deoxycytidine and 10 to 1000 mg of 2'-deoxythymidine. For example, the composition may comprise 13–1330 mg of 3',5'-diacetyl-2'-deoxyadenosine, 13–1310 mg of 3',3'-diacetyl-2'-deoxyguanosine, 14–1370 mg of 3',5'-diacetyl-2'-deoxycytidine and 14–1350 mg of 3',5'-diacetyl-2'-deoxythymidine. As is understood in the art, in calculating such dosages, the equivalent amount of the 2'-deoxyribonucleoside alone is considered, i.e., the acyl substituent and acid addition portion of any pharmaceutically acceptable salt are not included in the calculation.

For a suntan lotion, 0.1 to 5% by weight of the above compositions may be added. Generally, for this purpose, the acyl derivative will be in the form of the free acyl deoxyribonucleosides and not as the pharmaceutically acceptable salts.

There are some situations in which it is useful to deliver a single deoxyribonucleoside to tissues, e.g., deoxycytidine for treatment of toxicity caused by the antineoplastic drug arabinosyl cytosine, or thymidine for treatment of toxicity caused by methotrexate. In such cases, acyl derivatives of a single deoxyribonucleoside may be administered.

Methods of Preparation

When the acid source of the desired acyl derivative has groups which interfere with the acylation reactions, e.g., hydroxyl or amino groups, these groups may be blocked with protecting groups, e.g., t-butyldimethylsilyl ethers or t-BOC, groups, respectively, before preparation of the anhydride. For example, lactic acid may be converted to 2-t-butyldimethylsiloxypropionic acid with t-butyldimethylchlorosilane, followed by hydrolysis of the resulting silyl ester with aqueous base. The anhydride may be formed by reacting the protected acid with DCC. With amino acids, the N-t-BOC derivative may be prepared, using standard techniques, which is then converted to the anhydride with DCC. With acids containing more than one carboxylate group (e.g., succinic, fumaric, or adipic acid) the acid anhydride of the desired dicarboxylic acid is reacted with a 2'-deoxyribonucleoside in pyridine.

3',5'-Diacyldeoxythymidine may be prepared according to methods disclosed by Nishizawa et al., *Biochem. Pharmacol.* 14:1605 (1965), by treating deoxythymidine with 2.1 equivalents of an acid anhydride of the desired acyl compound in pyridine followed by heating to 80–85° C. for at least one hour. Alternatively, deoxythymidine may be treated with 2.1 equivalents of an acid chloride in pyridine at room temperature. (See Example 1.).

The 5'-hydroxyl group of deoxythymidine may be selectively acylated with 1 equivalent of the acid anhydride of the desired acyl compound in pyridine, which is heated to 80–85° C., according to Nishazawa, et al. Alternatively, the acid chloride (1 equivalent) may be reacted with deoxythymidine in pyridine and DMF at room temperature according to Baker et al., *J. Med. Chem.* 21:1218 (1978). (See Example 2.)

The 3'-hydroxyl group of deoxythymidine may be selectively acylated by selectively forming the 5'-O-t-butyldimethylsilyl derivative with 1.2 equivalents of t-butyldimethylchlorosilane in DMF containing imidizole, followed by acylation of the 3'-hydroxyl group with the appropriate acid anhydride, and cleavage of the 5'-t-butyldimethyl silyl ether according to Baker et al. (See Example 3.)

3',5'-Diacyldeoxycytidine may be prepared according to a method adapted from Gish et al., J. Med. Chem. 14:1159

(1971), by treating deoxycytidine hydrochloride with 2.1 equivalents of the appropriate acid chloride in DMF. (See Example 5.)

The 5'-hydroxy group of deoxycytidine may be selectively acylated by treating deoxycytidine hydrochloride with 1.1 equivalents of the appropriate acid anhydride in DMF. Gish et al. (See Example 6.)

The 3',5'-diacyl derivative of deoxyadenosine may be prepared by treatment with 2.1 equivalents of the appropriate acid chloride in DMF. (Adapted from Gish et al., see Example 7.)

The 5'-hydroxyl group of deoxyadenosine may be selectively acylated by treatment of deoxyadenosine hydrochloride with 1.1 equivalents of the desired acid chloride in DMF. (Adapted from Gish et al., see Example 8.)

3',5'-Diacyl-2'-deoxyguanosine may be prepared by treating deoxyguanosine hydrochloride with 2.1 equivalents of the appropriate acid chloride in DMF. (Adapted from Gish et al., see Example 9.)

The 5'-hydroxyl group of deoxyguanosine may be selectively acylated by treatment of deoxyguanosine hydrochloride with 1.1 equivalents of the appropriate acid chloride in DMF. (Adapted from Gish et al., see Example 10.)

Amino acids may be coupled to the exocyclic amino groups of deoxyadenosine, deoxycytidine, and deoxyguanosine (or 3' or 5' acyl derivatives thereof) by standard methods using dicyclohexylcarbodiimide. (See Example 11.)

These acyl compositions may be administered chronically to an animal which is at risk of either exposure to radiation, sunlight or chemical mutagens. The acyl compositions of the invention may also be administered after exposure to radiation, sunlight or chemical mutagens or after a wound is inflicted to enhance the repair of DNA and thereby to ameliorate the damage and promote survival of the animal. Advantageously, the compositions of the invention may be administered before or after radiotherapy or chemotherapy to ameliorate undesired side effects of the treatment.

The acyl compositions of the invention may also be coadministered with other radioprotective compounds such as WR-2721, NAC, DDC, cysteamine, 2-mercaptoethanol, mercaptoethylamine, dithiothreitol, glutathione, 2-mercaptoethanesulfonic acid, WR-1065, nicotinamide, 5-hydroxytryptamine, 2-beta-aminoethyl-isothiouronium-Br-Hbr, glucans, GLP/BO4, GLP/BO5, OK-432, Biostim, PSK, Lentinan, Schizophyllan, Rhodexman, Levan, Mannozym, MVE-2, MNR, MMZ, IL-2, TNF, thymic factor TF-5, glutathione peroxidase, superoxide dismutase, catalase, glutathione reductase, glutathione transferase, selenium, $CdCl_2$, $MnCl_2$, Zn acetate, vitamin A, beta carotene, prostaglandins, tocopherol, and methylene blue. The administration of these protective compounds along with the acyl derivatives of the invention provides protection greater than if the acyl derivatives or the other agents were given alone.

The pharmacologically active acyl derivatives may be combined with suitable pharmaceutically acceptable carriers comprising excipients and auxiliaries which facilitate processing of the active compounds. These can be administered as tablets, dragees, capsules, and suppositories. The compositions can be administered orally, rectally, vaginally, or released through the buccal pouch of the mouth, and may be applied in solution form by injection, orally or by topical administration. The compositions may contain from about 0.1 to 99%, preferably from about 50 to 90% of the active compound(s), together with the excipient(s).

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compound(s) with solid excipients, optionally grinding the resulting mixture and processing the mixture of granules, after adding suitable auxiliaries, if desired or necessary, to obtain tablets or dragee cores.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellulose, hydroxypropylmethyl cellulose, sodium carboxymethyl cellulose and/or polyvinyl pyrrolidone.

Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dye stuffs or pigments may be added to the tablets or dragee coatings, for example, for identification or in order to characterize different combinations of compound doses.

Other pharmaceutical preparations which can be used orally include push-fit capsules made of gelatin, as well as soft-sealed capsules made of gelatin and a plasticizer such as glycerol or sorbitol. The push-fit capsules contain the active compound(s) in the form of granules which may be mixed with fillers such as lactose, binders such as starches and/or lubricants such as talc or magnesium stearate, and, optionally, stabilizers. In soft capsules, the active compounds are preferably dissolved or suspended in suitable liquids such as fatty oils, liquid paraffin, or polyethylene glycols. In addition, stabilizers may be added.

Possible pharmaceutical preparations which can be used rectally include, for example, suppositories which consist of a combination of active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water soluble form, for example, water soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may include substances which increase the viscosity of the suspension which include, for example, sodium carboxymethylcellulose, sorbitol, and/or dextran. Optionally, the suspension may also contain stabilizers.

The acyl deoxyribonucleosides may be formulated as part of a skin lotion or suntan lotion for topical administration. Suitable formulations for topical administration include appropriate only suspensions or solutions. Suitable lipophilic solvents or vehicles include fatty oils, for example sesame oil or coconut oil, or synthetic fatty acid esters, for example ethyl oleate or triglycerides. These topical formulations may be used to treat damaged tissue such as skin wounds or burns, or to treat or prevent sunlight induced cellular damage (sunburn).

For purposes of enhancing wound healing, the compositions of the present invention may be formulated as part of wound dressings, or incorporated into bioerodible microcapsules for topical administration. Such microcapsules may comprise, for example, polylactate or lactate-glycolate copolymers. See Weise, D. L. et al., *Drug Carriers in Biology and Medicine*, Gregoriadis, G. et al., Academic Press, NY p. 237–270 (1979).

The following examples are illustrative, but not limiting of the methods and compositions of the present invention. Other suitable modifications and adaptations of a variety of conditions and parameters normally encountered in clinical therapy which are obvious to the those skilled in the art are within the spirit and scope of this invention.

EXAMPLES OF METHODS TO PREPARE COMPOUNDS OF THE INVENTION

Example 1

Preparation of 3',5'-Diacyl-2'-deoxythymidine

From acid anhydrides:

2'-Deoxythymidine is dissolved in anhydrous pyridine at room temperature. 2.1 molar equivalents of the acid anhydride of the desired acyl compound (e.g., acetic anhydride, lactate anhydride, butyric anhydride, etc.) is then added. The reaction mixture is then heated to 80–85° C. for 1 to 4 hours, cooled poured into ice water, and the esters recovered by extraction with chloroform or a similar solvent. The chloroform is then washed with ice-cold 0.01 N sulfuric acid, 1% aqueous sodium bicarbonate, and finally water. After drying with sodium sulfate, the chloroform is evaporated and the residual oil or crystals are subjected to chromatography (adapted from Nishizawa et al., *Biochem. Pharmacol.* 14:1605 (1965)).

From acid chlorides:

To 2'-deoxythymidine dissolved in anhydrous pyridine is added, at 5° C., 2.1 molar equivalents of the acid chloride of the desired acyl compound (e.g., palmitoyl chloride, acetyl chloride, etch.). The mixture is held at room temperature overnight, added to ice water, and worked up as indicated above (adapted from Nishizawa).

Example 2

Preparation of 5'-Acyl-2'-deoxythymidine

To 2'-deoxythymidine dissolved in anhydrous pyridine is added, at room temperature, 1.0 molar equivalent of the acid anhydride of the desired acyl compound. The reaction is then heated to approximately 80–85° C. for several hours, cooled, poured into ice water, and the esters recovered by extraction with chloroform or a similar solvent. The chloroform is then washed in ice-cold 0.01 N sulfuric acid, 1% aqueous sodium bicarbonate, and finally water. After drying with sodium sulfate, the chloroform is evaporated and the residual oil or crystals are subjected to chromatography. The major product, which is isolated by chromatography is the 5' substituted ester (adapted from Nishizawa et al.)

Alternatively, selectively 5' acylation of deoxythymidine may be accomplished by suspending 2'-deoxythymidine in a mixture of pyridine and N,N-dimethylformamide cooled to 0° C. in an ice bath. 1.0 molar equivalent of the acid chloride of the desired acyl compound is added dropwise to the mixture, which is stirred at 9° C. for 12–24 hours. Water is then added to stop the reaction, and then the solvents are evaporated in vacuo at 50° C. The residue is dissolved in methanol and purified by chromatography on silica gel (adapted from Baker et al., *J. Med. Chem.* 21:1218 (1978)).

Example 3

Preparation of 3'-Acyl-2'-deoxythymidine

To a stirred suspension of 2'-deoxythymidine in dry N,N-dimethylformamide is added 2.4 molar equivalents of imidazole followed by 1.2 molar equivalents of t-butyldimethylchlorosilane. The mixture is stirred with protection from moisture at room temperature for 20 hours, at which time the solvent is removed at 50° C. in vacuo. The residue is dissolved in 15 ml of ethyl acetate, washed, and evaporated to give a syrup from which is obtained, by crystallization from hot chloroform by the addition of hexane to the point of opalescence, 5'-(t-butyldimethylsilyl)-2'-deoxythymidine.

To a stirred suspension of 5'-(t-butylmethylsilyl)-2'-deoxythymidine in dry pyridine cooled to 0° C. is added 1.1 molar equivalents of the appropriate acid anhydride of the desired acyl compound, and the mixture is stirred with protection from moisture for 20 hours at 0–5° C., at which time the reaction is terminated by addition of a few ml of water. The solvent is evaporated and the residue is extracted and evaporated to give a thick, clear syrup, which is then dried in vacuo at 25° C.

The t-butylmethylsilyl group is removed with glacial acetic acid and tetrabutylammonium fluoride in tetrahydrofuran, yielding the desired 3'-acyl-2'-deoxythymidine derivative (adapted from Baker et al.).

Example 4

Preparation of $N^3$-Acyl-2'-deoxythymidine

The acylation of the secondary amine in the 3 position of the pyrimidine ring is accomplished by reacting 3',5'-diacyldeoxythymidine with 1.1 molar equivalents of the acid chloride of the desired acyl substituent in an aprotic solvent (such as ether, dioxane, chloroform, ethyl acetate, acetonitrile, pyridine, dimethylformamide, and the like) in the presence of 1–5 molar equivalents of an organic base (especially aromatic amines such as pyridine, trialkylamines, or N,N-dialkylanilines) (adapted from Fuji et al., U.S. Pat. No. 4,425,335). The acyl substituent on the secondary amine can be the same or different from those on the hydroxyl groups of the ribose moiety.

Example 5

Preparation of 3',5'-Diacyl-2'-deoxycytidine

2-Deoxycytidine hydrochloride is dissolved in N,N-dimethylformamide. 2.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents.

The oil is then triturated with 1N sodium hydrogen carbonate. The crystalline solid is collected, washed with water, dried, and recrystallized (adapted from Gish et al., *J. Med. Chem.* 14:1159 (1971)).

Example 6

Preparation of 5'-Acyl-2'-deoxycytidine

2-Deoxycytidine hydrochloride is dissolved in N,N-dimethylformamide. 1.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 7

Preparation of 3',5'-Diacyl-2'-deoxyadenosine

2'-Deoxyadenosine is dissolved in N,N-dimethylformamide and pyridine (1:1). 2.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized.

Example 8

Preparation of 5'-Acyl-2'-deoxyadenosine

2'-Deoxyadenosine is dissolved in N,N-dimethylformamide and pyridine (1:1). 1.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized.

Example 9

Preparation of 3',5'-Diacyl-2'-deoxyguanosine

2'-Deoxyguanosine is dissolved in N,N-dimethylformamide and pyridine (1:1). 2.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized.

Example 10

Preparation of 5'-Acyl-2'-deoxyguanosine

2'-Deoxyguanosine is dissolved in N,N-dimethylformamide and pyridine. 1.1 molar equivalents of the acid chloride of the desired acyl substituent is added, and the mixture is stirred overnight at room temperature. The reaction mixture is concentrated in vacuo to an oil, and triturated with a mixture of ethyl acetate and diethyl ether or similar solvents. The oil is then triturated with 1N sodium hydrogen carbonate. The crystalline solid is collected, washed with water, dried, and recrystallized (adapted from Gish et al.).

Example 11

Synthesis of N-lysyl-5'-O-palmitoyl-deoxycytidine

5'-O-palmitoyldeoxycytidine is synthesized by reacting deoxycytidine hydrochloride with 1.1 equivalents palmitoyl chloride in dry dimethylformamide.

14 grams of 5'-O-palmitoyl-deoxycytidine is dissolved in 100 ml dimethylacetamide, 1 molar equivalent of di-tert-butoxycarbonyl-lysine is added, and the mixture is cooled in an ice bath. 1.2 molar equivalents (7.4 g) of dicyclohexyl-carbodiimide are added and the mixture is stirred at 4° C. for 90 hours. The precipitate dicyclohexylurea) is removed by filtration. 100 ml of water is added to the filtrate, followed by 1 liter of ethyl acetate. $N^4$-(di-N-tert-butoxycarbonyl-lysyl)-5'-O-palmitoyl-deoxycytidine is separated from unreacted reagents by chromatography over silica gel. The t-butoxycarbonyl protecting groups are removed by the standard methods of treatment with an acid, such as trifluoroacetic acid.

Similarly, 5'-O-acyl or 3',5'-O-diacyl derivatives of deoxycytidine, deoxyadenosine, or deoxyguanosine in general may have lysine or arginine coupled to their exocyclic primary amino groups with dicyclohexylcarbodiimide.

Examples of Protection of Nucleosides

From Enzymatic Degradation by Acylation

Deoxyribonucleosides are rapidly degraded following administration to animals. In order to successfully utilize acylated nucleosides to deliver nucleosides to tissues, it is imperative that acylation should prevent degradation of the nucleoside moiety by the enzymes that normally degrade the nucleosides. For each of the major deoxyribonucleosides, a different enzyme is involved in the first step of their degradation. The first step in degradation of deoxyadenosine is deamination catalyzed by adenosine deaminase. Thymidine is initally catabolized by thymidine phosphorylase; deoxyguanosine by purine nucleoside phyosphorylase, and deoxycytidine is degraded by deoxycytidine deaminase.

Example 17

Solutions (100 micromolar in phosphate-buffeed saline) of each of the deoxyribonucleosides or their acylated derivatives were incubated at 37° C. with each of the four enzymes: adenosine deaminase (ADA), cytidine deaminase (CDA), purine nucleoside phosphorylase (PNP), and thymidine phosphorylase (TP). Enzymatic degradation of compounds was determined by HPLC.

TABLE 1

Protection of Deoxyribonucleosides
From Enzymes Which Catalyze
Initial Steps of Degradation
By 5'-0-Acylation

| Compound | Enzyme | | | |
|---|---|---|---|---|
| | ADA | CDA | PNP | TP |
| deoxyadenosine | + | − | − | − |
| 3',5'-di-O-acetyldeoxyadenosine | − | − | − | − |
| 5'-O-palmitoyldeoxyadenosine | − | − | − | − |
| deoxycytidine | − | + | − | − |
| 3',5'-di-O-acetyldeoxycytidine | − | − | − | − |
| 5'-O-palmitoyldeoxycytidine | − | − | − | − |
| deoxyguanosine | − | − | + | − |
| 3',5'-di-O-acetyldeoxyguanosine | − | − | − | − |
| 5'-O-palmitoyldeoxyguanosine | − | − | − | − |
| thymidine | − | − | − | + |
| 3',5'-di-O-acetylthymidine | − | − | − | − |
| 5'-O-valerylthymidine | − | − | − | − |
| 5'-O-octanoylthymidine | − | − | − | − |
| 5'-O-palmitoylthymidine | − | − | − | − |
| 5'-O-valerylthymidine | − | − | − | − |

+ indicates that compound was a substrate for the enzyme.
− indicates that compound was not a substrate for the enzyme.

These data show that 5'-O-acylation of deoxyribonucleosides protects them from the enzymes that catalyze the initial steps of their degradation. Thus, the nucleoside moiety of acylated nucleosides will remain intact in vivo until deacylation occurs.

Examples of Deacylation of Acylated Deoxyribonucleosides in Liver Extracts

Acylated deoxyribonucleosides were incubated with rat liver extracts in order to asses the relative rates of enzymatic deacylation of derivatives with different substituents, and to determine whether different nucleosides with the same substituents are deacylated at similar rates. Deacylation of the derivatives of the invention in vivo results in release of the parent nucleosides, which can then be utilized by cells.

Example 12

Whole rate livers were homogenized in phosphate-buffered saline (10 ml per gram of liver) and centrifuged. The supernatant was diluted to a final concentration of 50 ml buffer per gram of liver, and stock solutions of acylated deoxyribonucleosides were added so that the compounds were present at concentrations of 100 micromolar. 100 microliter aliquots were removed periodically to determine, by HPLC, the amounts of free nucleosides produced as a function of time.

TABLE 2

| Compound | Nucleosides Released (namomoles/ml) Hours | | | | |
|---|---|---|---|---|---|
| | 1 | 2 | 3 | 8 | 24 |
| 3',5'-di-O-acetyldeoxyadenosine | 26 | 39 | 57 | | |
| 3',5'-di-O-acetyldeoxycytidine | 25 | 40 | 50 | | |
| 3',5'-di-O-acetyldeoxyguanosine | 23 | 43 | 63 | | |
| 3',5'-di-O-acetylthymidine | 19 | 40 | 63 | | |
| 5'-O-valerylthymidine | 47 | 95 | 98 | | |
| 5'-O-octanoylthymidine | 74 | 84 | 96 | | |
| 5'-O-acetyldeoxyadenosine | 48 | | | | |
| 5'-O-valerydeoxyadenosine | 65 | | | | |
| N-acetyldeoxycytidine | 0 | 0 | 0 | 0 | |
| N-valeryldeoxyguanosine | 0 | 0 | 0 | 0 | |
| N-palmitoyldeoxyguanosine | 0 | 0 | 0 | 0 | |
| 5'-di-O-palmitoyldeoxyadenosine | | | | 5 | 16 |
| 5'-di-O-palmitoyldeoxycytidine | | | | 4 | 15 |
| 5'-di-O-palmitoyldeoxyguanosine | | | | 3 | 14 |
| 5'-di-O-palmitoylthymidine | | | | 4 | 14 |

These data indicate that in liver extracts, di-O-acetyl derivatives of each of the four deoxyribonucleosides are deacylated at very similar rates. This is also true for 5'-O-palmitoyl derivatives, although the palmitoyl substituents are cleaved at a much slower rate than are the acetate groups. This suggests that the rate of deacylation of O-substituted deoxyribonucleosides is primarily a function of the nature of the acyl substituent, and not the nucleoside to which it is attached. This is important in the practice of the invention, since some therapeutic effects are obtained only when derivatives of more than one nucleoside are coadministered. It is preferably if deacylation of different nucleosides in a therapeutic mixture occurs at similar rates in vivo because optimal proportions of nucleosides are delivered to tissues simultaneously. The large variation in deacylation rates for nucleosides substituted with short chain (acetyl) versus long chain (palmitoyl) fatty acids gives rise to the opportunity for selecting acyl substituents according to the rates of deacylation (or rates of nucleoside delivery) required in different clinical situations. Midlength fatty acid substituents (e.g., valeryl and octanoyl) are cleaved more rapidly than are shorter (acetate) or longer (palmitate) substituents.

In this same liver extract, deoxyribonucleosides per se are rapidly degraded, e.g., deoxyadenosine at a concentration of 100 micromolar is entirely degraded, initially by deamination to form inosine, within 2 minutes. Thus, it can be understood that following administration, the O-acylated deoxyribonucleosides of this invention will gradually release, and provide to tissues, free nucleosides for a sustained period of time, compared to the brief period of nucleoside availability following administration of the parent deoxyribonucleosides themselves. Fatty acids on the primary amines of either the pyrimidine ring of deoxycytidine or the purine rings of deoxyguanosine are not removed at an appreciable rate by liver enzymes.

Examples of Oral Administration of Acylated Nucleosides

In order to demonstrate delivery of deoxyribonucleosides after oral administration of acylated nucleosides, plasma thymidine levels were measured after oral administration of either 3',5'-di-O-acetylthymidine or thymidine itself.

Example 13

Male F344 rats (350 g) were implanted with chronic jugular vein catheters for blood sampling and allowed to recover for two days. A basal blood sample was taken, and then 0.7 millimoles of thymidine or 3',5'-di-O-acetylthymidine (DAT) were administered by gavage. Blood samples were withdrawn at 0.5, 1, 2, and 4 hours after administration, centrifuged, and the supernatant (plasma) was deproteinized with methanol. The concentration of thymidine in the plasma samples was determined by HPLC with UV absorbance detection.

The basal plasma thymidine concentration was 1 micromolar. Following oral administration of thymidine, plasma thymidine levels reached a maximum of 9 micromolar one hour after administration and returned to basal concentrations by 4 hours. In contrast, following oral administration of an equimolar dose of 3',5'-di-O-acetylthymidine, plasma thymidine concentrations reached a maximum of 80 micromolar within 30 minutes, and were still elevated above basal values four hours after administration.

Thus, oral administration of di-O-acetylthymidine delivers much greater quantities of tymidine to tissues (over a longer duration) than does administration of the nonderivatized nucleoside as is shown in FIG. 4 wherein the comparative data are plotted.

Examples of Clinical Administration Radiation Exposure

Three situations wherein acyl derivatives of deoxyribonucleosides may be clinically useful in treating radiation damage are 1) accidental exposure to ionizing radiation, as in a nuclear accident; 2) exposure to X-radiation during radiography; and 3) radiotherapy of cancer.

In the first case, acyl deoxyribonucleoside derivatives should be administered in a formulation suitable for parenteral injection, followed by oral administration several times per day of doses equivalent to 0.5 to 2 grams of each of the four major deoxyribonucleosides. It is essential that the derivatives of all of the nucleosides be coadministered.

In the second case, X-ray exposure during diagnostic radiography, acyl deoxyribonucleside derivatives are given orally before and after exposure.

In the third case, during cancer radiotherapy, the acyl ribonucleoside derivatives are particularly useful in restoring bone marrow function after its undesirable but unavoidable suppression during irradiation. Moreover, in formulations designed to selectively deliver nucleosides to normal but no neoplastic tissues, the acyl nucleoside derivatives will improve the therapeutic index (ratio of efficacy to toxicity) of the radiation treatment. Similar doses of deoxyribonucleoside derivatives may also be used to treat bone marrow suppression caused by antineoplastic or antiviral chemotherapy.

The following example discloses the benefits of the invention in the treatment of irradiated mice.

Methods

Balb/c+ mice were subjected to gamma irradiation (Cobalt 60) at a dose rate of 7.3 Rads/min. The field was measured twice by Fricke dosimetry to ensure field uniformity and dose constancy for each mouse. Groups of 15 mice received total doses of gamma radiation of 675, 700, 725, and 750 R.

Mice were divided into four treatment groups (5 mice at each radiation dose), each receiving a different post-irradiation treatment:

Group 1: 0.9% saline (control group);
Group 2: A mixture of deoxyribonucleosides (equimolar mixture of deoxyadenosine, deoxyguanosine, deoxycytidine, and thymidine);
Group 3: A mixture of the 3,5'-di-O-palmitoyl derivatives of deoxyadenosine, deoxyguanosine, deoxycytidine, and thymidine, equimolar to the doses of nonderivatized nucleosides.
Group 4: A mixture of the 5'-O-acetyl derivatives of deoxyadenosine, deoxyguanosine, deoxycytidine, and thymidine. (Tested at 750 R only.

The nucleosides or di-O-acetyl derivatives were administered by intraperitoneal injection (8 micromoles/0.2 ml physiological saline three times daily (every 8 hours) for 4 days, beginning 30 minutes after irradiation). Mice in the control groups received injections of 0.2 ml physiological saline on the same schedule. Mice receiving 5'-O-palmitoyl nucleoside derivatives were given 8 micromoles only once per day for the 4 days following irradiation; thus, they received only one third of the molar quantity of nucleosides given to the mice receiving either nonderivatized or acetylated nucleosides.

Mortality was monitored daily for 30 days.

Results and Discussion

The LD 50/30 (the radiation dose that produces 50% mortality within 30 days after irradiation) in this strain of mice is approximately 650 R. At the radiation doses tested, death occurred, if at all, 12 to 20 days after irradiation, which is characteristic of lethal post-irradiation bone-marrow failure.

At the lowest radiation dose tested in this experiment (675 R), only 20% of the saline-treated control mice survived; no control animals survived at any of the higher radiation doses (Table 1). Post-irradiation administration of deoxyribonucleosides did not significantly improve survival over that of mice in the control group. In contrast, animals treated with the di-O-acetyl deoxyribonucleosides after irradiation survived radiation doses which were lethal to animals given either deoxyribonucleosides or saline (700 R through 750 R). Mice treated with 5'-O-palmitoyl deoxyribonucleosides also survived radiation doses that were lethal to untreated mice (750 R). It is apparent that the palmitoyl derivatives (8 micromoles administered once per day) are at least as effective in improving survival of irradiated mice as a threefold higher dose of di-O-acetyl nucleosides (8 micromoles administered three times per day).

Agents that improve survival when administered after irradiation do so by improving proliferation and differentiation of surviving hematopoietic stem cells. It is therefore apparent that the nucleoside derivatives of the invention will be useful in other situations of bone marrow impairment, such as occurs after treatment with certain antineoplastic agents.

TABLE 3

Percentage of mice surviving at 30 days after potentially lethal gamma irradiation

| Treatment | Radiation Dose (R) | | | |
|---|---|---|---|---|
| | 675 | 700 | 725 | 750 |
| | % Survival at 30 Days | | | |
| saline (control) | 20 | 0 | 0 | 0 |
| deocyribonucleosides | 40 | 0 | 0 | 0 |
| di-O-acetyldeoxyribonucleosides | 100 | 100 | 100 | 80 |
| 5'-O-palmitoyl-deoxyribonucleosides | — | — | — | 100 |

Mice were treated with the listed agents after gamma irradiation as described in the text.

Wound Healing

In promoting the healing of skin wounds (whether surgical incisions or accidental wounds), it is best to apply acyl deoxyribonucleoside derivatives topically, either in an ointment, in bioerodible microcapsules, or incorporated into wound dressings. A topical antibiotic might be coadministered. The molar equivalent of 2 to 20 mg of a mixture of all four major deoxyribonucleosides should be applied per square cm of wound area, or 1 to 10 mg per cm of linear incision. The onset of the earliest phases of wound healing in particular is accelerated.

Liver Regeneration

Acyl derivatives of deoxyribonucleosides are useful in promoting regeneration of damaged or diseased liver, particularly for accelerating regrowth after surgical removal of a portion of the liver. In this case, oral administration of the derivatives is preferable, in doses corresponding to the molar equivalents of 0.2 to 2 grams of each nucleoside. It is important that derivatives of all four major deoxyribonucleosides be coadministered.

What is claimed is:

1. A method of enhancing the delivery of exogenous 2'-deoxyadenosine to the tissue of an animal, comprising the step of administering to said animal of an acyl derivative of 2'-deoxyadenosine, having the formula

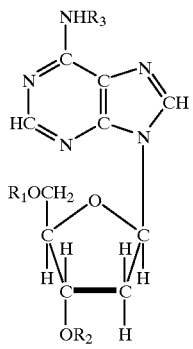

1 wherein $R_1$, $R_2$ and $R_3$ are the same or different and each of H or an acyl group derived from a carboxylic acid, provided that at least one of $R_1$, $R_2$ and $R_3$ is not hydrogen.

2. A method as in claim 1 wherein $R_1$, $R_2$, and $R_3$ are the same or different and each is hydrogen or an acyl group derived from (a) an unbranched fatty acid with 2 to 22 carbon atoms, (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine, (c) nicotinic acid, or (d) a dicarboxylic acid having 3 to 22 carbon atoms, provided that not all of $R_1$, $R_2$, and $R_3$ are H, or a pharmaceutically acceptable salt thereof.

3. A method as in claim 2 wherein $R_1$, $R_2$ and $R_3$ are the same or different and each is H or an acyl group derived from an unbranched fatty acid with 2 to 22 carbon atoms.

4. A method as in claim 3 wherein $R_1$ and $R_2$ are fatty acids with 6 to 16 carbon atoms.

5. A method of enhancing the delivery of exogenous 2'-deoxyguanosine to the tissue of an animal, comprising the step of administering to said animal an acyl derivative of 2'-deoxyguanosine having the formula

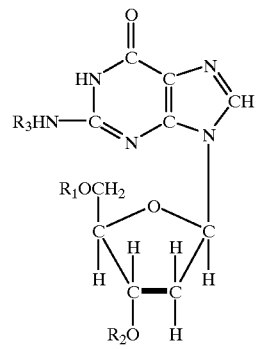

2 wherein $R_1$, $R_2$ and $R_3$ are the same or different and each is H or an acyl group derived from a carboxylic acid, provided that at least one of $R_1$, $R_2$ and $R_3$ is not hydrogen.

6. A method as in claim 5 wherein $R_1$, $R_2$, and $R_3$ are the same or different and each is hydrogen or an acyl group derived from (a) an unbranched fatty acid with 2 to 22 carbon atoms, (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, phenylalanine, carnitine, and ornithine, (c) nicotinic acid, or (d) a dicarboxylic acid having 3 to 22 carbon atoms, provided that not all of $R_1$, $R_2$, and $R_3$ are H, or a pharmaceutically acceptable salt thereof.

7. A method as in claim 2 wherein $R_1$, $R_2$ and $R_3$ are the same or different and each is H or an acyl group derived from an unbranched fatty acid with 2 to 22 carbon atoms.

8. A method as in claim 3 wherein $R_1$ and $R_2$ are fatty acids with 6 to 16 carbon atoms.

9. A method of enhancing the delivery of exogenous 2'-deoxycytidine to the tissue of an animal, comprising the step of administering to said animal an acyl derivative of 2'-deoxycytidine, having the formula

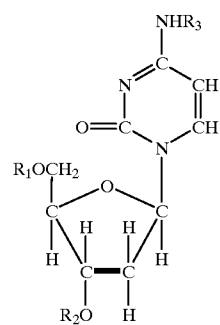

3 wherein $R_1$, $R_2$ and $R_3$ are the same or different and each is H or an acyl group derived from a carboxylic acid, provided that at least one of $R_1$, $R_2$ and $R_3$ is not hydrogen.

10. A method as in claim 9 wherein $R_1$, $R_2$, and $R_3$ are the same or different and each is hydrogen or an acyl group derived from (a) an unbranched fatty acid with 2 to 22 carbon atoms,
   (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
   (c) nicotinic acid, or
   (d) a dicarboxylic acid having 3 to 22 carbon atoms, provided that not all of $R_1$, $R_2$, and $R_3$ are H, or a pharmaceutically acceptable salt thereof.

11. A method as in claim 2 wherein $R_1$, $R_2$ and $R_3$ are the same or different and each is H or an acyl group derived from an unbranched fatty acid with 2 to 22 carbon atoms.

12. A method as in claim 3 wherein $R_1$ and $R_2$ are fatty acids with 6 to 16 carbon atoms.

13. A method of enhancing the delivery of exogenous 2'-deoxythymidine to the tissue of an animal, comprising the step of administering to said animal an acyl derivative of 2'-deoxythymidine, having the formula

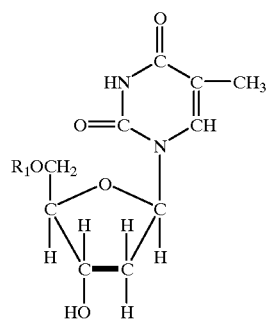

4 wherein $R_1$ is an acyl group derived from (a) an unbranched fatty acid with 2 to 15 or 17 to 22 carbon atoms,
   (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
   (c) nicotinic acid, or
   (d) a dicarboxylic acid having 3 to 22 carbon atoms, or a pharmaceutically acceptable salt thereof.

14. A method as in claim 13 wherein $R_1$ is an unbranched fatty acid with 2 to 15 or 17 to 22 carbon atoms.

15. A method as in claim 14 wherein $R_1$ is an unbranched fatty acid with 2 to 4 carbon atoms.

16. A method of enhancing the delivery of exogenous 2'-deoxythymidine to the tissue of an animal, comprising the step of administering to said animal an acyl derivative of 2'-deoxythymidine, having the formula

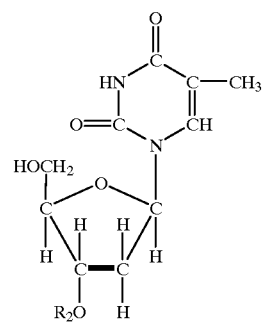

5 wherein $R_2$ is an acyl group derived from (a) an unbranched fatty acid with 2 to 13 or 15 to 22 carbon atoms,
   (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
   (c) nicotinic acid, or
   (d) a dicarboxylic acid with 3 to 22 carbon atoms, or a pharmaceutically acceptable salt thereof.

17. A method as in claim 16 wherein $R_2$ is an unbranched fatty acid with 2 to 13 or 15 to 22 carbon atoms.

18. A method as in claim 17 wherein $R_2$ is an unbranched fatty acid with 2 to 4 carbon atoms.

19. A method of enhancing the delivery of exogenous 2'-deoxythymidine to the tissue of an animal, comprising the step of administering to said animal an acyl derivative of 2'-deoxythymidine, having the formula

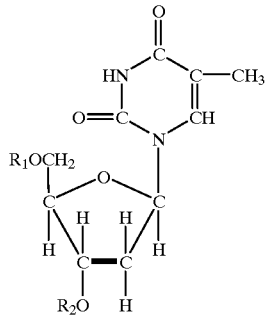

6 wherein $R_1$ and $R_2$ are the same or different and each is an acyl group derived from (a) an unbranched fatty acid with 2 to 22 carbon atoms,
   (b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
   (c) nicotinic acid, or
   (d) a dicarboxylic acid with 3 to 22 carbon atoms, or a pharmaceutically acceptable salt thereof.

20. A method as in claim 19 wherein $R_1$ and $R_2$ are the same or different and each is an unbranched fatty acid with 2 to 22 carbon atoms.

21. A method as in claim 20 wherein $R_1$ and $R_2$ are the same or different and each is an unbranched fatty acid with 2 to 4 carbon atoms.

22. A method of enhancing the delivery of exogenous 2'-deoxythymidine to the tissue of an animal, comprising the step of administering to said animal an acyl derivative of 2'-deoxythymidine, having the formula

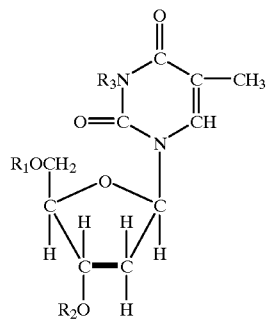

wherein $R_1$ and $R_2$ are the same or different and each is an acyl group derived from (a) an unbranched fatty acid with 2 to 22 carbon atoms,
(b) an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, carnitine, and ornithine,
(c) nicotinic acid, or
(d) a dicarboxylic acid with 3 to 22 carbon atoms, and $R_3$ is an acyl group derived from an optionally substituted benzoyl or heterocyclic acid that is substantially nontoxic, or a pharmaceutically acceptable salt thereof.

23. A method as in claim 22 wherein $R_1$ and $R_2$ are the same or different and each is an unbranched fatty acid with 2 to 22 carbon atoms.

24. A method as in claim 23 wherein $R_1$ and $R_2$ are the same or different and each is an unbranched fatty acid with 2 to 4 carbon atoms.

25. A method as in claim 23 wherein $R_3$ is an acyl group derived from nicotinic acid, benzoic acid, or para-aminobenzoic acid.

* * * * *